United States Patent
Chaudhary et al.

(10) Patent No.: US 6,777,591 B1
(45) Date of Patent: Aug. 17, 2004

(54) LEGUME-LIKE STORAGE PROTEIN PROMOTER ISOLATED FROM FLAX AND METHODS OF EXPRESSING PROTEINS IN PLANT SEEDS USING THE PROMOTER

(75) Inventors: Sarita Chaudhary, Calgary (CA); Gijs van Rooijen, Calgary (CA); Maurico Moloney, Calgary (CA); Surindor Singh, Downer (AU)

(73) Assignees: SemBioSys Genetics Inc., Calgary (CA); Commonwealth Scientific and Industrial Research Organisation (CSIRO), Campbell (AU)

( * ) Notice: Subject to any disclaimer, the term of this patent is extended or adjusted under 35 U.S.C. 154(b) by 177 days.

(21) Appl. No.: 09/645,593

(22) Filed: Aug. 25, 2000

Related U.S. Application Data

(60) Provisional application No. 60/161,722, filed on Oct. 27, 1999, and provisional application No. 60/151,044, filed on Aug. 27, 1999.

(51) Int. Cl.[7] .......................... A01H 5/00; C12N 15/82
(52) U.S. Cl. .................... 800/298; 435/320.1; 435/419; 435/468; 538/24.1; 800/278; 800/281; 800/287
(58) Field of Search ................................ 800/278, 281, 800/287, 298, 306, 312, 314, 317.3, 320, 320.1–320.3; 435/468, 419, 320.1; 536/24.1, 23.6, 23.1

(56) References Cited

FOREIGN PATENT DOCUMENTS

WO   WO 98/18948   * 5/1998

OTHER PUBLICATIONS

Donald et al 1990, The EMBO Journal 9(6):1717–1726.*
Reeck et al 1987, Cell 50:667.*
Chamberland et al 1992, Plant Molecular Biology 19:937–949.*
Borgmeyer, J.R. et al. *Biochemical and Biophysical Research Communications* (1992) vol. 187, No. 1, 480–487.
Sammour, R.H., *Bot. Bull. Acad. Sin.* (1990) 40:121–126.

* cited by examiner

Primary Examiner—David T. Fox
Assistant Examiner—David H Kruse
(74) Attorney, Agent, or Firm—Bereskin & Parr; Micheline Gravelle

(57) ABSTRACT

Novel methods for the expression of non-native genes in flax seeds and the seeds of other plant species are provided. The methods involve the use of seed-specific promoters obtained from flax. Additionally provided are novel flax seed-specific promoters, chimeric nucleic acid constructs comprising novel flax seed-specific promoters, transgenic plant cells, transgenic plants and transgenic plant seeds containing novel flax seed-specific promoters. The promoters and methods are useful, for example, for altering the seed oil and protein composition in flax seed or other plant seeds.

16 Claims, 24 Drawing Sheets

FIGURE 1A

```
   1 ttcaaaacccgattcccgaggcggccctattgaagatatggggaagttcgacgagatcgatgtgcggtcgagtgctatg    80
  81 gtgatggtgccgtttggggaggatgagcgagatagccaagactagcattccgttccacacagagttggaatttgta    160
 161 ccaaatccaacacttgtcgtattggagcgacgataggacgcggaaaaacacatccgttggatcaggagttgtacgatg    240
 241 atctcgagccttatgtgtcgaagaatccgaggtatgcttacgtgaactacagggatctcgacatcggatgaatggagga    320
                R1
 321 ggtgaagggatgagaagggtacttatggtgaggctaagtgtggggggagaagtactttgggtcaactttgatcggtt    400
                                                                            R2
 401 ggttcgggtgaagacgattgttgatccaataatgtgtttcgaaacgagcagagcattccctcaattccaactcggttat    480
 481 aaggatcaatgatcaatgagaattttcctttccaatgtgattacaagttctattgggtcagctttctcaactgctcctat    560
 561 tcatttagattaattcataacaactattaatttaccagcctttatccgcccgttgccgattatttctttaagtttt    640
 641 agatgaaatgaaaccgatttagttttttattgagatgagattaatcttaattgcttgaaatttactcacggttgatgtga    720
                                                      I1
 721 tatttggaattaactaaaatgataatcggataaaaatattaaaataaaatattaaaataacataagaacaata    800
                                                          R3
 801 aaataaataaatttaatttatttcctgttttcttattctgtatcatcatctctcttacttcttaaaggctt    880
              I1                                                           R4
              R4
 881 ttcaattatcacttaattaatataataatataattcattattaatcgttaattctataacattaattttttaattataaagttatgcggtcagtt    960
                                                                                R5
 961 caatatgatataatataataattcaattgtttctgcggtctccttgtagttctgcggtataacgactcggagcgacgagcctttgct   1040
                                                                    R1
1041 tctgcaagctccgagctccttgtcatcgttagttctgcggtctcaagtataacgactcggagcgacgagcctttgct   1120
1121 tccaatggacggttgcatttctgcgtcgtcgattgcgtgagctcgatgcgtgtcatgctgagtcagagttcctacaaaaaac   1200
1201 cctaaactagagggtgattaggggtgaattaggggtgcctggttgtggcctggttccttgtccaaagtttttagtcaacttaaaaac   1280
1281 agacttaaattttatgcttcaaaatagtttatctgttattattagcgtgtaattagtcttgacaatgggccggacgg   1360
```

FIGURE 1B

```
1361 gtacggattcgggaccccgatcccgccatagtgtaatgctcaactgccaagtcagcattggaccgaaattattggac 1440
1441 acgaagtactaatgtgaaaaactttacatttgttatttctactttaatactatgtcatttttcaaaatttgaactttaat 1520
                                                                          R6
1521 actatgtttttatatagtttagtatatcttaatttttatgcaaattcatctaattgtattaaactatttcgatccgtag 1600
             R3
1601 ctaattatttcgaaggcaagtcaaagtcttattgtggactatgtgagctaatatattgaacctttatctctcccaacactc 1680
1681 aagttaattgaaccaaactcgatcggttgggtttcgagctattcgagccattgttgttatatgcacgtgagatatcaag 1760
                            R2
1761 attgaccgaacactttattgataatgtagaaaaagaaaacatattctaagactacatgcatgcaaagtcaaccccct 1840
                                                  I2
1841 gcatgaaagctgctcaacacgtggcatagactcccgccacgtgtccattccacctcatcacctcaccccaccgttcac 1920
              CACA     ABRE
1921 ctcttattatatcacaacaatcaatcctactcctccatactcgaacaaatcgaccaactttatacaattcccca 2000
               TATA         R5                                              CAT
2001 aacttgattaatttctcagcaat ATG GAT CAG ACA CAC CAG ACA TAC GCC GGA ACC ACG CAG AAC 2065
   1                        M   D   Q   T   H   Q   T   Y   A   G   T   T   Q   N   14
2066 CCG AGC TAT GGC GGG GGC ACA ATG TAC CAG CAG CAG CCG AGG TCT TAC CAG GCG 2125
  15  P   S   Y   G   G   G   T   M   Y   Q   Q   Q   P   R   S   Y   Q   A   34
2126 GTG AAG GCG GCC ACT GCA GCC ACC GCG GGT GGA TCC CTC ATC GTT CTG TCC ATC 2185
  35  V   K   A   A   T   A   A   T   A   G   G   S   L   I   V   L   S   I   54
2186 CTT ACG GCC ACC GTC ATT TCA CTC ATC ATA GCC ACC CCT CTC CTC GTC ATC TTC AGC CCT 2245
  55  L   T   A   T   V   I   S   L   I   I   A   T   P   L   L   V   I   F   S   P   74
2246 GTT CTT GTC CCG GCT CTC ATC ACC GTC TTG CTC ATC ACC GGG TTT CTT GCT TCC GGT 2305
  75  V   L   V   P   A   L   I   T   V   L   L   I   T   G   F   L   A   S   G   94
2306 GGG TTC GGA GTC GCC GCC GTC ACC GTC TTG TCC TGG ATC TAT AG gtatgtataagctttggactt 2370
  95  G   F   G   V   A   A   V   T   V   L   S   W   I   Y   R                       109
2371 tagtattgttataaatacataagtgattatgaacatgatctcccaacaagagttatttaatgcattctcggtctg 2450
```

FIGURE 1C

```
2451 actcgatcggtgggttttgagctactcggtcacaatggtcgggtcggctctgatctgttatactaatatttggaagcc 2530

2531 tgaagtttcattgttctgcccaacttccccactaccctttgagggtgttaagaagccatacaaactaattatgaatccct 2610

2611 cccaacaactcagaactcgagtcagtgggttgtgacggttctctataaacatttcgaaaatctttgttcaatgaacgtag 2690

2691 aaatgaccatgcttgatgattgtgggtcttataag G TAC GTG ACC GGC GGG CAC CCG GCG GGA GGG 2756
                                          Y   V   T   G   G   H   P   A   G   G   119

2757 GAT TCG CTG GAC CAG GCT AGG TCG AAG CTG GCC GGA AAG GCC AGG GAG GTG AAG GAC AGG 2816
 120  D   S   L   D   Q   A   R   S   K   L   A   G   K   A   R   E   V   K   D   R  139

2817 GCG TCG GAG TTC GCA CAG CAG CAT GTC ACA GGT GGT CAA CAG ACC TCT TAA agagagtcctct 2879
 140  A   S   E   F   A   Q   Q   H   V   T   G   G   Q   Q   T   S   *              156

2880 agttaaattggtctctcgttctgttcgtgcgcgcttgtaaactctctttaagtgtgctgttttccttttgtctcgtgt 2959

2960 gttgtaagtgaaagtgtaatcgaagttccaagttggagatgtttgtaacgatgatgttttctaataatcagagatattaa 3039
                                                                       Poly A signal 3040 aagggttgctaatttagtattgcgtctgatctcggaccaaactcgcaagtaaaattgcagaggatgagttgtacagaaca 3119

3120 agcgtgcattgttctgaagttcatctcctggagccgacctgttgcttgcagttcgcaagtccactagacaatgtt 3199

3200 acgagttaagcctctgtcaaacagatcgctcagcgtcccagaaaacaccagattttcgaaaaccatcggggatcaatt 3279

3280 ttcgattcaattccgatcttggaagtacttgaacagaagcatgatgctaaaagataataagaaatcgaagcctagaaaag 3359

3360 ttgtacagaagcaacaagtcgactaaacagaaacagcagcttcacctgaatgaaggagctttgatcaatcctagcttcat 3439

3440 gttaacagaagtcgactaaacagaaacagcagcttcacctgaatgaaggagctttgatcaatcctagcttcat 3519

3520 tcccctttgaaattgcagacagagctctcatcctgctaaagctggtggcttattcttaaccctgcaatcaataagcatga 3599

3600 actaacattggacaccttcatcggcgattgctcgaaatcagtgagcgagggattacctgtgtgtgtagtaacctctc 3679
```

FIGURE 1D

```
3680  tccttgtacataaatctggaaattccggcatcaactactgccacctttctgcttaagtgatttatcaccaaggctga  3759
3760  gcgtgattccttgcgtcttgctccgaatcctgatgtatccactgagctttccatctccttcctccaggcttatgttc  3839
3840  accaatgcgtcctcgccgaacacactcttggctacaagttcgcagccaggaatccacactctccatcaagtgcagacct  3919
3920  gcaaacccaaataagaacacaaactccaaagtcaacgatcaattctccgccttttatgaagaaaggaaacttctgggt  3999
4000  acttacggtgccgtcagacacttcatatttgtagacttgatgatatggtccaggaattccttctcgttctgaattgttgt  4079
4080  gttaacagcaacctgacagacagaaagatatcgcaaattaagatactgggatgactaggcacagagaaatgaaatctaa  4159
4160  ttctagaagtaaaccttatttcccattcaaattctgcccacatagtccgaacgcagcatccgagcaagaagcaggag  4239
4240  agatgtaatccatgatatcgatgtggatatcgttgaggacgacaactgaacgttccatcacattgg  4305
```

FIGURE 2A

```
   1 tctagacatttgacataaaccgaattcaaagaacacaacattgactaaccacaaaagaaatagagtagtgaaatttgga   80
                      R1
  81 agattaaaaatagaaacaaactgattcttagaagagatgattaggtgcttcagttcggtctgtcaggaatcga  160
                   R2
 161 gatgttcacttattacattgtcgattcatctcccaattgtcctggttcctttactgtccgacgcttttttgaatcccag  240
                         R3
 241 ttaattcccatcaagtcttccttcagctgcgtagcactgctagctccaacatggagcgtggagtctactcgttcatgggg  320
 321 catcgcaaaggtttgccttcatgttctgctaccagcagcgcccaccgcctcttggttgtgtggacaattgcggtgaagc  400
 401 gcgcaagttgacatcccatagtctcgacacttcaccatatgatgtttaaaacgtatcacgagtgcgatctacatgtc  480
 481 ccatcaccaccacatataaagcaatagtttgggagcttttcatatttgaaacgggcattgacgacttgccctctcgataat  560
 561 ttaatctttttttctcttcagctgattgtgtgcatccattcgggctcagtgaagtttcctaatgtgcgagctacaggtt  640
 641 attgggtcgtgtcgtatgatgatacgaagcagtcgatgaagtttcctaatgtgcgagctccgcaaagaacccgcga  720
 721 ggtagatcgtatgctagtacccaaaaatcagtttgtcgtagcggaatcaacactagagactcaccctaatgcatctcatg  800
 801 tgtgatgaacagtttatcattgtgagtctagggtgcattgtgatgaccaatgcacattgagcttatgatagaatttg  880
                                              R3
 881 aataggaagcgttttccaccgatcacgaaatagctacccctttttcgggcgccaaattccggcatcctatcttccacc  960
 961 acaacttaaagatgcgatcggtaaggaactcaccgaataatcttcggtgaccggttcctgttgatca 1040
1041 agtccctcaattcctcaacctagtcttcaatcgccgctagcgttatccccgcatatgggacttcatagcgcggagcgt 1120
1121 agccggagacgacgagcaagaaggatgagcggcggcagattgcggctaaagaaacgagcttcctgccttgctctatggag 1200
1201 gcagatttctgagttgatggtgatggattgtgatgtggacactttaattaagttgattttttagcacttcattcacg 1280
1281 taattaaataaatttccagtattttatattttattcctttacgttatctaattttttgaaagattaaaactttgatat 1360
                R4                                                                 R2
```

FIGURE 2B

```
1361 aggcaagatcatgacacgtcgaagttaagtgatgagactcctaacaagtaataacaagcagttcataaccgaatga 1440
1441 ccttgatcttactaagcttgagatcattgaacatataattaatgaaagataagaacttaatataaaat 1520
                                            R4
1521 cattcaaaacgagaaactgataacaaacaaagcaacggccaacaaaataatagacggtggaaggatgatgcagagcc 1600
1601 atccaccctttttcccagtttccttactgctcatctctctatgcatatcacaagacgcccttgaaacttgttagtcatg 1680
                                                                         R5
1681 cagagccctttactcgccaggtcaccgccaccacgtgttactctctatcacttcctcctttaaagaaccaccacgc 1760
      R5
1761 caactccctctcacaaacactcataaaaaaccaccctcttgcatttctcccaagttcaaattagttcacagctaagcaag 1840
1841 aactcaacaaca ATG GCG GAT CGT ACA ACA CAG CCA CAA GTC CAC ACC CAG CAC 1903
                  M   A   D   R   T   T   Q   P   H   Q   V   H   T   Q   H  17
                  1

1904 CAC TAT CCC ACC GGC GGG GCT TTC CGT TAT GAA GGT GGA CTC AAA GGC GGT CCA CAT 1963
     H   Y   P   T   G   G   A   F   R   Y   E   G   G   L   K   G   G   P   H  37

1964 CAC CAG CAA GGA TCA GGC AGC AGC GGG CCA GCT TCA AAG GTG TTA GCA GTC ATG ACC GCG 2023
     H   Q   Q   G   S   G   S   S   G   P   A   S   K   V   L   A   V   M   T   A  57

2024 CTC CCC ATC GGC ATC GGG ACC CTC CTT GCC ATA ACC TTG CTT CTT CTA GTC CCG GCC ATG ATC 2083
     L   P   I   G   I   G   T   L   L   A   I   T   L   A   L   V   P   A   M   I  77

2084 GGG CTG GCG ATC ACC ACC CCG ATT TTT GTC ATC TGC AGC CCT GTT CTA GTC GCC GGG ACA GGG GCC GCT 2143
     G   L   A   I   T   T   P   I   F   V   I   C   S   P   V   L   V   A   G   T   A  97

2144 CTG CTC ATC GGG TTT GCC GTG AGC GCG TTT CTG GCC ATG CAG GCT GGG CAG CTG ACA GTT GGA GTG 2203
     L   L   I   G   F   A   V   S   A   F   L   A   M   Q   A   G   Q   L   T   V   G  117

2204 CTG ACC TCG CTG TCG TGG TTT GCG AGG TAT CTG CAG CAG GCA CGC ATG CAG GCT GGA GTT GGA GTG 2263
     L   T   S   L   S   W   F   A   R   Y   L   Q   Q   A   R   M   Q   A   G   V  137

2264 GGG GTG CCG GAT AGT TTC GAG CAG GCG AAG AGG CGC ATG CAG GAT GCT GCT GGG TAT ATG 2323
     G   V   P   D   S   F   E   Q   A   K   R   R   M   Q   D   A   A   G   Y   M  157
```

FIGURE 2C

```
2324 GGG CAG AAG ACC AAG GAA GTT GGG CAG GAG ATC CAG AGG AAG TCT CAG GAT GTG AAA GCA 2383
158   G   Q   K   T   K   E   V   G   Q   E   I   Q   R   K   S   Q   D   V   K   A  177

2384 TCA GAC AAA TAA ggtgataataaggggttttgggttcgtgtgtaaactggtaaaatgaaattctgggtttactg 2459
178   S   D   K   *                                                                   181

2460 tactttgcatgtagtggaatgaatgagtcttgttctctttgtctttaatcataaagtaagaagcagcattcatgt 2539

2540 tctgttgaatattgtcaagaattcgcaacaaattagctaaaccagttcaatctaccggttagacgacttcccagtaa 2619

2620 gaaacattccaggtccatcccgtataagagtctggacttctgaaacctttagaccttggatttgaaaaagatgaaac 2699

2700 ctttagaataaattacaacgatggcagattgtacaaaactggagtcgagatcatgtaaattagcccataactaagaaccg 2779

2780 gcgatgacaacaattactaggaatatggttgttgggctgttcggcggtgatgatttggaagaatcgggatcc 2859

2860 agaatgtgagaaccgaatcatcgacgaacattaccggcgaggagcccatttcaagcaacttggaactcctatatggct 2939

2940 gttccagcaggccacctgctcaagaagaagccatgtcagaaatccttacgaaatctaactggatgctgatatgaa 3019

3020 tccgccaggtgtgcggagttctttacaggcaggatctataaagaaacatgttttgtattggcattgttgatgttcca 3099

3100 agcacgcagcgatctctccggatcctaacaacaaaatacgattctgtaagaaacaagcgcagaaaacttctgcaac 3179

3180 gaaaccactcgtgtatatttggttctgagttggagaaagatgaccatactgtatttggttgaactgtattggaaccga 3259

3260 aattttgagttgaaaagcgagtgatcgtatataaattcagattcagattaggatatcctatgagagaaggtagagttac 3339

3340 ctgatactacatactgccatcaggggtaaaagttgcctcgatggttgtgtttggagatggttccaggctaaatccacaa 3419

3420 cgctgaacaaattaaagatgaatgatcaatcttcaaccctacttctgcattatgaggattggctcaaggctctcta 3499

```
1    tccactatgtgtaggtcatatccatcattttaattttggcaccattcattcatcttgccttaggatgtgaatatga       80
     ─────────────                       ──────
      5' primer (1)                       AT rich
81   acggccaagtaagagaataaaatccaaattaaagcaagagaggccaagtaagataatccaaatgtacacttgtca      160
                                  ───────
                                   AT rich
161  tcgccgaaattagtaaaatacgcggcatattgtattcccacacattattaaaataccgtatatgtattggctgcattgc   240
241  atgaataatactacgtgtaagcccaaagaaccacgtgtagccatgcaaagttaacactcacgacccattcctcagt     320
                                         ──                ──
                                         RY                G box seed-specific
321  ctccactatataaaccaccatcccccaatcttaccaaaccaccacacgactactcacaactcgactctcacacctaaagaa  400
        ────                                                          ────────────
        TATA                                                          3' primer (1)
401  ccaatcaccaccacaaaaaaATGGCAAAGCTGATGAGCTTAGCAGGCCTAGCAACGCAGTTCCTCTTCCTGATCGTGGTGGAC  480
  1                      M  A  K  L  M  S  L  A  A  V  A  T  Q  F  L  F  L  I  V  V  D    21

481  GCATCCGTCCGAACCACAGTGATTATCGACGAGGAGACCAACCAAGGCCGCGTGGAGGCAAGGTGGCCAGGGAGGACAGCAGC  560
 22   A  S  V  R  T  T  V  I  I  D  E  E  T  N  Q  G  R  G  G  G  K  V  A  G  T  A  A    48

561  AGTCTGCGAGCAGCAGATCCAGATCCAGCAGCGAGACTTCCTGAGGAGCTGCCAGCAGTTCATGTGGGAGAAAGTCCAGAGGGCG  640
 49   V  C  E  Q  Q  I  Q  Q  R  D  F  L  R  S  C  Q  Q  F  M  W  E  K  V  Q  R  G  G    75

641  GCCACAGCCACTATTACAACCAGGGCCCGTGAGGAGGCGAACAGAGCCAGTACTTCGAACAGCTGTTTGTGACACTTA     720
 76   H  S  H  Y  Y  N  Q  G  R  G  G  G  E  Q  S  Q  Y  F  E  Q  L  F  V  T  T  L     101

721  AGCAATTGCGCACCGGTGCACCATGCCCAGGGACTTGAACGTGCCAAATGAGGCAGGAAATCCAGCAGCA      800
102   S  N  C  A  P  R  C  T  M  P  G  D  L  K  R  A  I  G  Q  M  R  Q  E  I  Q  Q  Q    128

801  GGGACAGCAGCAGGGACAGCAGGAAGTTCAGAGGTGGATCCAGCAAGCTAAACAAATGCTAAGGACCTCCCGGAC      880
129   G  Q  Q  Q  Q  Q  Q  Q  E  V  Q  R  W  I  Q  Q  A  K  Q  I  A  K  D  L  P  G  Q    155
```

FIGURE 3B

```
881  AGTGCCCGCACCCAGCCTAGCCAATGCCAGTTCCAGGGCCAGCAGCAATCTGCATGGTTTTGAagggtgatcgattatga  960
156   C   R   T   Q   P   S   Q   C   Q   F   Q   G   Q   Q   Q   S   A   W   F   *        5'primer (2)        175
961  gatcgtacaaagacactgctaggtgttaaggatgtgataatataatgagatgaatgtgttttaagttagtgtaa          1040
1041 cagctgtaataaagagagagagagagagagagagagagaggctgatgaaatgttat                            1120
1121 gtatgtttcttggttttaaaataaatgaaagcacatgtctgtggtctatcgaattattcggcggttcctgtgggaa       1200
1201 aaagtccagaagggcggccgcagctactactacaaccaaggccgtggaggagggcaacagagccagcacttcgatagctg   1280
1281 ctgcgatgatcttaagcaattgaggagcgagtgcacatgcagggactggagcgtgcaatcggccagatgaggcaggaca   1360
1361 tccagcagcaggacagcagcaggaagttgagaggttggtcccatcaatctaaacaagtcgctaggaccttccgggacag   1440
1441 tgcggcacccagcctagccgatgcagctccagggcagcagcagtctgcatgttttgaagtggtgatcgatgagatcg     1520
1521 tataaagacactgctaggtgttaaggatgggataataagatgtgttttaagtcattaaccgtaataaaagagagagagg   1600
1601 ctgatgaatgttatgtattgtatgtttctgttcttggttttaaaattaaatgaaagcacatgtctcgtgggttctatc    1676
                                                                  3'primer (2)
```

FIGURE 4A

```
         10         20         30         40         50         60         70         80         90        100
ctcaagcatacgacaagggtaaataacatagtcaccagaacataataacaaaaagtgcagaagcaagataaaaattagctatggacattcaggttc 110        120        130        140        150        160        170        180        190        200
atattggaaacatcattatcctagtcttgtgaccatccttcctcctgctctagttgagaggcttgggactaacgagaggtcagttggatagcagatcc 210        220        230        240        250        260        270        280        290        300
ttatcctggactagcctttctgtgttcagagtctcgtgccgcgtctacatctatctccattaggtctgaagatgactcttcacaccacgacgttt
                                                                              IR1

310        320        330        340        350        360        370        380        390        400
aaggtctctactcctagcttgcaataacctggcttgcaataccggagcatcgtgcacgatgattggatactgtggaggagtgtttgctgatt
                                                       IR1

410        420        430        440        450        460        470        480        490        500
tagagctcccggtggggtgattgacttcgattcagtttaggcttgaaattttcaggttccattgtgaagccttagagcttgagcttccttcca 510        520        530        540        550        560        570        580        590        600
tgttaatgccttgatcgaattctcctagagaaaagggaagtcgatctctgagtattgaaatcgaagtgcacatttttttcaacgtgtccaatcaatcca
                  IR2                                 IR2

610        620        630        640        650        660        670        680        690        700
caaacaaagcagaagacaggtaatcttcatactgacaagtaatagtctccacgtcatgcataataacgtctcgttcctcaagagggttttc 710        720        730        740        750        760        770        780        790        800
cgacatccataacgaccgagcctcatgaaagcattagggaagaacttttggtctcttcttgtcatggcctttataggtgtcagcgagctcgccaattc 810        820        830        840        850        860        870        880        890        900
ccgtccgactggctccgcaaaatattcgaacggcaagttatgacttgcaaccataactccacgtattgagcaggacctattgtgaagactcatctcat 910        920        930        940        950        960        970        980        990       1000
ggagcttcagaatgtggttgtcagcaaccaatgacgcaactcatcacatgacggacgtccagtgggtgagcgaaacaggaagcgcctatcttt 1010       1020       1030       1040       1050       1060       1070       1080       1090       1100
cagagtcgtgagctccacaccggattccgcaactacgtgggcaggcttcgccgtattagagatatgttgaggcaagaccatctgtgccactcgta 1110       1120       1130       1140       1150       1160       1170       1180       1190       1200
caattacgagagttgtttttttgatttcctaagttctctcgttgatggtgagctcatattctacatcgtatggtctctcaacgtcgtttcctgtcat
```

FIGURE 4B

```
      1210       1220       1230       1240       1250       1260       1270       1280       1290       1300
ctgatatcccgtcatttgcatccacgtgccgcgcctcccgtgccagtgtccctagtgtcatgcatgcacgccaaattggtggtggtgcgggctgcctgtgctt
                    ABRE 1310       1320       1330       1340       1350       1360       1370       1380       1390       1400
cttaccgatgggtggaggttgagtttggggtctccgcggcgatggtagtgggttgacggttggtgtggttgacggcattgatcaattacttcttgc
                                                                              R1

1410       1420       1430       1440       1450       1460       1470       1480       1490       1500
ttcaaattctttggcagaaaacaattcattagattagaactgaaaccagagtgatgagaacgaggattaagtcagattccaacagagttacatctcttaaga
                                                                          R1

1510       1520       1530       1540       1550       1560       1570       1580       1590       1600
aataatgtaaccccctttagactttatatatttgcaattaaaaataattaactttagactttatatagttttaataactaagttaaccactcta
                R2                                                     R2

1610       1620       1630       1640       1650       1660       1670       1680       1690       1700
ttatttatatcgaaactatttgtatgtctcccctcaaataaacttggtattgtgtttacagaacctataatcaaataatcaatactcaactgaagtttg 1710       1720       1730       1740       1750       1760       1770       1780       1790       1800
tgcagttaattgaagggattaacggccaaaatgcactagtattatcaaccgaatagattcacactagatggccattttccatcaatatcatcgccgttctt 1810       1820       1830       1840       1850       1860       1870       1880       1890       1900
ctttctgtccacatatcccctgaaacttgagagacacctgactcattgtccttattacgtgttacaaaatgaaaccatgcatccatgcaaactgaa
                                                                                          Legumin Vicilin 1910       1920       1930       1940       1950       1960       1970       1980       1990       2000
gaatggcgcaagaaccctttccctccattctctatgtggcgaccatccaattcaccatcccgctataaacacccccatcacttcacctagaacatca
                                                                    CAAT       TATA 2010       2020       2030       2040       2050       2060       2070       2080       2090       2100
tcactacttgctatccatccaaagataccaccATGGCTAGATCATCAAGCCCTTTGCTTCTCTCACTCTGCATTTTCGCCATTCTTCTTCCACTCTTC
                                 M  A  R  S  S  S  P  L  L  L  S  L  C  I  F  A  I  L  F  H  S  S
                                 Signal sequence 2110       2120       2130       2140       2150       2160       2170       2180       2190       2200
TCTGGGTAGGCAGCAATTCCAGCAGGGGAACGAGTGCCAGATCGACAGGATCGACGATCGAGCCGGACAAAACCATCCAGGCAGCAGAAGCTGGCACCATC
 L  G  R  Q  Q  F  Q  Q  G  N  E  C  Q  I  D  R  I  D  A  S  E  P  D  K  T  I  Q  A  E  A  G  T  I 2210       2220       2230       2240       2250       2260       2270       2280       2290       2300
GAGGTATGGGACCAGAACCGCCAGCAATTCCAGTGCCTGGTGTTGCCGTTGCCGTTGTGCCGTTGAAGGCGCACCATTGAGCCCAAAGGTCTTCTTGCCTTTCTACAGCA
 E  V  W  D  Q  N  R  Q  Q  F  Q  C  A  G  V  A  V  V  R  R  T  I  E  P  K  G  L  L  P  F  Y  S
```

FIGURE 4C

```
      2310        2320        2330        2340        2350        2360        2370        2380        2390        2400
ACACCCCTCAGCTCCATCTACATCGTTCAAGgtataaattaaatcagttcatacaatgataaccaccacttgaatgtattatcaaatatcaatgatcga
 N  T  P  Q  L  I  Y  I  V  Q 2410        2420        2430        2440        2450        2460        2470        2480        2490        2500
tgcacctgtgtatgtgttgtgtatattcagGTAGGGAGTTACAGGAATCATGTTCCAKGATGTCCAGAGACATTCGAGGAATCCCAGCAGCAAGACAAC
                               G  R  G  V  T  G  I  M  F  P  X  C  P  E  T  F  E  E  S  Q  Q  Q  G  Q 2510        2520        2530        2540        2550        2560        2570        2580        2590        2600
AGGGCCAACAGGGTAGTTCCCAAGACCACCAGACGACCACCAGAAGATCCGCCGCTTCCGTGAAGGTGACGTCATTGCCGTCCTGCCGTGTAGCCACTGGTCCTA
 Q  G  G  Q  Q  G  S  S  Q  D  D  Q  H  Q  K  I  R  R  F  R  E  G  D  V  I  A  V  P  A  G  V  A  H  W  S  Y 2610        2620        2630        2640        2650        2660        2670        2680        2690        2700
CAACGATGGCAACGAACCAGTCATGGCCATTGTTGTCCATGACACTTCCAGCCACCTCAACCTGGACAACAACCCCAGgtatataagcattgccgt
 N  D  G  N  E  P  V  M  A  I  V  V  H  D  T  S  S  H  L  N  Q  L  D  N  N  P  R 2710        2720        2730        2740        2750        2760        2770        2780        2790        2800
agttgctaataattgcacacaattgaactctatttcagtatctaataacttttcctttttggcagAACTTCTACTTGGCAGGAAACCCGAGAGAC
                                                                   N  F  Y  L  A  G  N  P  R  D 2810        2820        2830        2840        2850        2860        2870        2880        2890        2900
GAGTTCGAACAATCGCAGCAAGGAGCAGGCTGAGCCGTGGGAGAGTGAAGGTGGACGAGGACGCGCAGGAACCCTCTTCAACCTGCAACAACCTCTTCTT
 E  F  E  Q  S  Q  Q  G  G  R  L  S  R  G  E  S  E  G  G  R  R  E  P  L  Q  P  A  T  T  S  S 2910        2920        2930        2940        2950        2960        2970        2980        2990        3000
GCCGGAATCGACTCCAAGCTCATCGCGGAGGCGTTCAATGTCGACGAGAACGTGGCAAGGAGGCTACAGAGAGCAGACAGGAGGCCAGATCGTCCG
 C  G  I  D  S  K  L  I  A  E  A  F  N  V  D  E  N  V  A  R  R  L  Q  S  E  N  D  N  R  G  Q  I  V  R 3010        3020        3030        3040        3050        3060        3070        3080        3090        3100
AGTCGAAGGCGAGCTCGACATCGTCAGACCTCCGACCAGTATCCAGGAGGAGTCACAGGAGCAGGAGTCGTGGTGCCGCTACTCCAATGGA
 V  E  G  E  L  D  I  V  R  P  P  T  S  I  Q  E  E  S  Q  E  Q  G  G  R  G  G  G  R  Y  Y  S  N  G 3110        3120        3130        3140        3150        3160        3170        3180        3190        3200
GTGGAGGAGACCTTCTGCTCCATGAGACTTCTCGGGCAGACATTTCACTCCAGAAGCCGGCGTTAGATCCCTCA
 V  E  E  T  F  C  S  M  R  L  I  E  N  I  G  D  P  S  R  A  D  I  F  T  P  E  A  G  R  V  R  S  L
```

FIGURE 4D

```
      3210       3220       3230       3240       3250       3260       3270       3280       3290       3300
ACAGCCACAACCTCCCCGTCCTGCAATGGATCCAGCTTAGCGCCGAGAGAGGCGTTCTCTACAATgtatagatctcactcacgcaccaactctaaattga
 N  S  H  N  L  P  V  L  Q  W  I  Q  L  S  A  E  R  G  V  L  Y  N
      3310       3320       3330       3340       3350       3360       3370       3380       3390       3400
atccctaattatttaattcaccgatatctgaccgaccggttgaatttgtagGAAGCGATCAGGCTGCCGCACTGGAACATCAACGCACACAGCATAGT
                                                    E  A  I  R  L  P  H  H  W  N  I  N  A  H  S  I  V
      3410       3420       3430       3440       3450       3460       3470       3480       3490       3500
GTACGGCGATCAGAGGACAAGCCAGAGTCCAGATCGTGAACGAGGAAGGAATTCGTGTTCGATGGAGTGCTGCAGGAAGGACAGGTGGTGACGGTGCCG
 Y  A  I  R  G  Q  A  R  V  Q  I  V  N  E  E  G  N  S  V  F  D  G  V  L  Q  E  G  Q  V  V  T  V  P
      3510       3520       3530       3540       3550       3560       3570       3580       3590       3600
CAGAACTTCGCGGTGGTAAAGAGATCCCAGAGCGAGAGATTTGAGTGGGTGGCGTTCAAGACCAACGCGATGGTGAACTCGCTAGCCGGGAGGA
 Q  N  F  A  V  V  K  R  S  Q  S  E  R  F  E  W  V  A  F  K  T  N  D  N  A  M  V  N  S  L  A  G  R
      3610       3620       3630       3640       3650       3660       3670       3680       3690       3700
CATCGGCAGTAAGGGCGATCCCCGCGATGTACTGGCTAACGCCTGAGGGTGTCGCCGGAGAGGGCGAGGTGAAGTTCAACAGGCAGGAGACTCA
 T  S  A  V  R  A  I  P  A  D  V  L  A  N  A  W  R  V  S  P  E  E  A  R  R  V  K  F  N  R  Q  E  T  H
      3710       3720       3730       3740       3750       3760       3770       3780       3790       3800
CTTGGCTAGCACCAGGGGCCAGTCCAGGTCGCCCCGGGAGGTTGAATGTCGTCAAGGAGGTGATCAACTTGCTTATGTAAaatgtgacggtgaaataataa
 L  A  S  T  R  G  Q  S  R  S  P  G  R  L  N  V  V  K  E  V  I  N  L  L  M  *
      3810       3820       3830       3840       3850       3860       3870       3880       3890       3900
cggtaaaatatgtaataataataaagccacaaagtgagaatgaggggaaggaaatgtgtaatgagccagtagccggtggtgtctaattttg
      3910       3920       3930       3940       3950       3960       3970       3980       3990       4000
tatcgtattgtcaataaatcatgaattttgtggttttttaaatcatgaatttttaaatttataaaataatcccaatcggaagaacaac
      4010       4020       4030       4040       4050       4060       4070       4080       4090       4100
attccatatccatgatgttttctttaccaaatcagttcttgagaggatgaagcatcaacagttctgcaactatccctcaaaagtttaaaatga
      4110       4120       4130       4140       4150       4160       4170       4180       4190       4200
acaacaaggaacagagcaacgttccaaagatcccaaacgaaacatattctctaatactactaataattattactgccgaatcacaatcccct
```

FIGURE 4E

```
         4210      4220      4230      4240      4250      4260      4270      4280      4290      4300
gaatgattcctattaactacaagccttgttggcggcgagaagtgatcggcgcggagaagcagcggactcggagacgaggccttggatgagcagagtc 4310      4320      4330      4340      4350      4360      4370      4380      4390      4400
tttacctgcgccagggcgtgaagggggaagagagcggccttctggagtaggagttcagcaagcaagcggcgttccttggcggagtaagcggacgtaaggggtggntgtc 4410      4420      4430      4440      4450      4460      4470      4480      4490      4500
gacgtcntcgtttcnggaggcgnattcatgaagggttaaagtcanatctgtagctctcgagtgctcaggagccnaaagacgttggaaaccgtcgncgt 4510      4520      4530      4540      4550      4560      4570      4580      4590      4600
ttgggcatcagtcngcggggcacgcttccctcctgctgctccanaancnangtnagtnagtnatattaaagaaatnatattaaagagattaatgaatattaagaatnannaggagg 4610      4620      4630      4640      4650      4660      4670      4680      4690      4700
attgnaacggtcngancggtcannaggaaanagtttttannggtttaaatactgggggagtngnagccngcccnctggttccngtgtagangaaaccaagnnccgg 4710      4720      4730      4740      4750      4760      4770      4780      4790      4800
gaggnttncannngnnaggagaaaaggganncatttnannangcngagggacatgaacngtaacngagctgnggttcannnancggcgnnnggnagtcc 4810      4820      4830      4840      4850      4860      4870      4880      4890      4900
cnnggaccnggntggggtnanaaggganaaggaacattggtngnangganaanaccnttttacnattgcctttgcaggnnngtntnggcncntncgggt 4910      4920      4930      4940      4950      4960      4970      4980      4990
nacatnccgctgcatggctttgggngccnanaggnagcccnanggnanncngcccncttgtncangncgctnaagttcnattgtanatggncgttg
```

FIGURES 9A-C
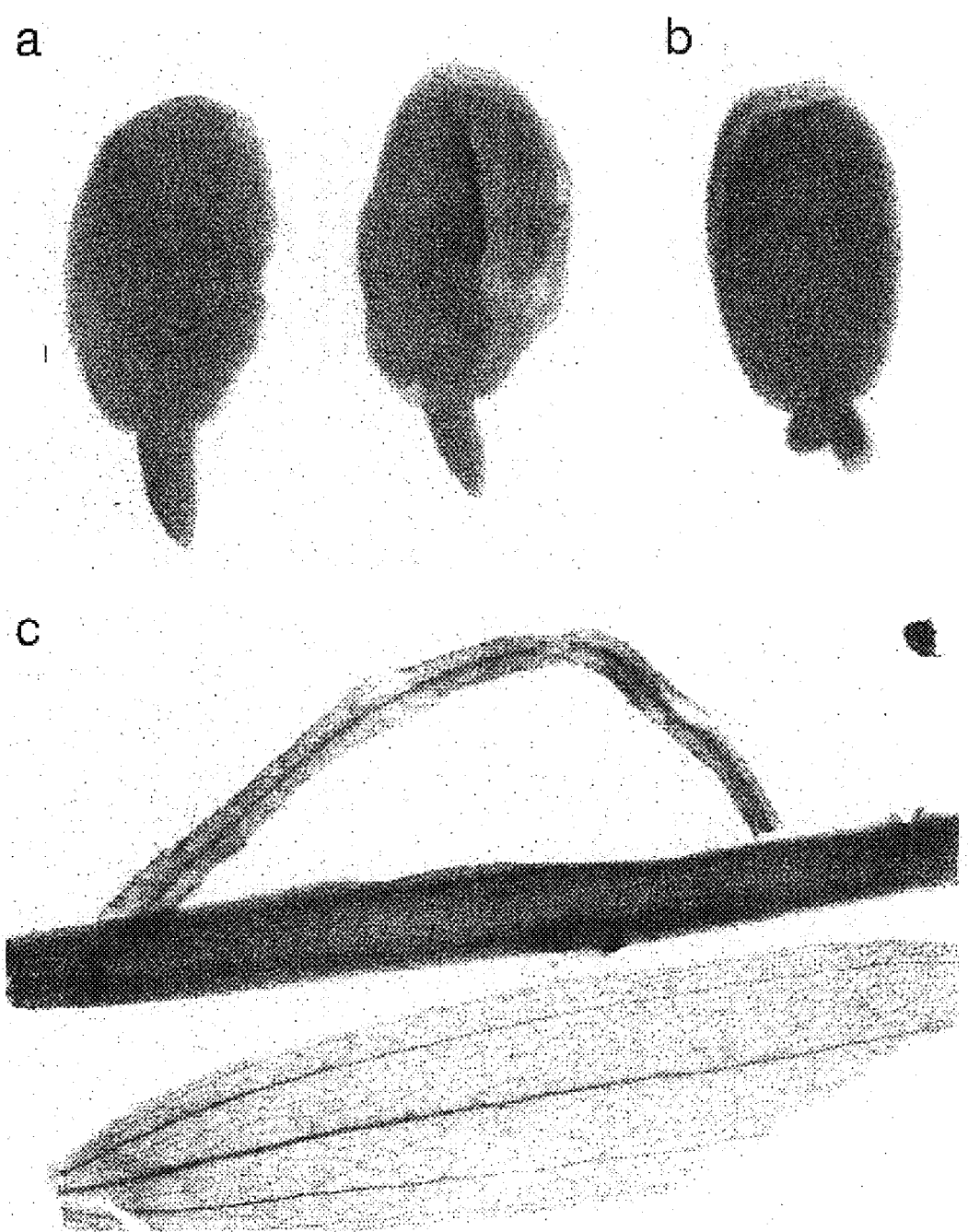

LEGUME-LIKE STORAGE PROTEIN PROMOTER ISOLATED FROM FLAX AND METHODS OF EXPRESSING PROTEINS IN PLANT SEEDS USING THE PROMOTER

This application claims benefit from U.S. provisional application No. 60/151,044, filed Aug. 27, 1999 and U.S. provisional application No. 60/161,722 filed on Oct. 27, 1999, both of which are incorporated herein by reference.

FIELD OF THE INVENTION

The present invention relates to plant genetic engineering methods useful for the alteration of the constituents of plant seeds. More specifically, the invention relates to promoters that have been obtained from flax and are capable of directing expression of non-native genes in flax seeds as well as the seeds of other plants.

BACKGROUND OF THE INVENTION

Flax or linseed (*Linum usitatissimum*) is a commercially important oilseed crop. Flax oil and meal are valuable raw materials derived from flax seed. A further economically significant raw material, flax fiber, is obtainable from the stem of the plant. The flax oil fraction is used for non-edible purposes, for example in the manufacture of varnish and paint, and has more recently become suited for use in the manufacture of a range of edible products, such as margarines and salad oils and dressings, by virtue of newly bred so called Linola cultivars (Green (1986) Can. J. Plant Sci, 66: 499–503). Flax meal is used primarily as a constituent of ruminant feeds while flax fibers are used in the manufacture of linen fabrics. Given its economic importance as a source for raw materials, it is desirable to further improve and diversify the available flax cultivar portfolio both with respect to agronomic performance, for example seed yield, resistance to pathogens and low climatic temperatures, and with respect to yield and quality of the raw materials to suit downstream applications. Although it is possible to obtain improved flax cultivars through conventional plant breeding, as evidenced by the development of the Linola cultivars, developing an elite agronomic plant line requires large investments in plant breeding due to the long timelines involved. Plant genetic engineering technology allows the isolation of genes directly from unrelated species and the transfer of these genes into elite agronomic backgrounds, thereby significantly reducing the time required to develop new cultivars. In addition plant genetic engineering permits the manufacture of products not naturally obtainable from flax, for example therapeutic agents.

In order to develop novel flax cultivars through plant genetic engineering, control over the expression of the introduced foreign or non-native gene is of critical importance. The desired expression characteristics for the non-native gene, such as the level of expression of the non-native gene, the particular plant tissue or organ in which the non-native gene is expressed, and the particular time in the growth cycle of the plant at which the non-native gene is expressed, will vary depending on the application for which the plant line is developed. For example, the modification of the seed oil composition may require low levels of seed-specific expression of an enzyme involved in fatty acid metabolism at an early stage in seed development (see for example U.S. Pat. No. 5,420,034). On the other hand expression of a pharmaceutical protein could preferably require high levels of leaf-specific expression upon harvesting of the plant leaves (see for example, U.S. Pat. No. 5,929,304).

In order to manipulate the expression characteristics of non-native genes numerous factors can be influenced. One factor is the choice of the transcriptional promoter used. A wide range of plant compatible promoters is currently available and some of the better documented promoters include constitutive promoters such as the 35S CaMV promoter (Rothstein et al. (1987), Gene 53: 153–161) and the ubiquitin promoter (U.S. Pat. No. 5,614,399), tissue specific promoters such as seed-specific promoters, for example the phaseolin promoter (Sengupta-Gopalan et al., (1985), PNAS USA 82: 3320–3324) and inducible promoters, such as those inducible by heat (Czarnencka et al., (1989), Mol. Cell. Biol. 9 (8): 3457–3464), UV light, elicitors and wounding (Lois et al., (1989) EMBO J. 8 (6): 1641–1648), or chemicals such as endogenous hormones (Skriver et al. (1991), Proc. Natl. Acad. Sci. USA 88(16): 7266–7270). Other factors that can be manipulated in order to control the expression characteristics of non-native gene in plants include transcriptional modification factors such as introns, polyadenylation sites and transcription termination sites. The expression characteristics of the non-native gene can further be manipulated by factors that affect translation, such as ribosomal binding sites and the codon bias that is exhibited by the host. Furthermore, the non-native gene itself may affect the viability of the transgenic plant, thus limiting particularly the levels of expression that can be attained. In some cases it may be possible to overcome this problem, by expressing the protein in a tissue specific manner, e.g. in the leaves or seed, or by restricting the accumulation of the protein in different subcellular compartments such as for example the cytoplasm, the endoplasmic reticulum or vacuoles, typically by the presence or the absence of specific targeting sequences capable of directing the protein to these compartments. Another factor that will affect the expression characteristics is the location in which the construct inserts itself into the host chromosome. This effect could provide an explanation as to why different plants, transformed with the same recombinant construct, can have fluctuating levels of recombinant protein expression.

To the best of the inventors' knowledge, expression of non-native genes in flax seeds is only documented in PCT Patent Aplication WO 98/18948. This application discloses two stearoyl-acyl carrier protein desaturase (SAD) genes derived from flax. The associated SAD promoter sequences are useful for the modification of flax and other plants for the expression of endogenous or foreign genes. However the methods taught by WO 98/18948 are limited by the fact that the SAD promoters are not seed-specific in flax and confer expression to leaves, stems, flowers and seeds. Expression of non-native genes thus may result in undesirable side effects in non-seed tissues. In addition the use of the SAD promoters allows limited control over expression level and timing of expression.

There is a need in the art to further improve methods for the expression of non-native genes in flax seeds and other plant seeds.

SUMMARY OF THE INVENTION

The present invention relates to improved methods for the seed-specific expression of non-native genes in plants. In particular, the invention relates to improved methods for the seed-specific expression of non-native genes in flax.

Accordingly, in one aspect, the invention provides a method for the expression of a nucleic acid sequence of interest in flax seeds comprising:

(a) preparing a chimeric nucleic acid construct comprising in the 5' to 3' direction of transcription as operably linked components (1) a seed-specific promoter obtained from flax; and
(2) the nucleic acid sequence of interest wherein said nucleic acid of interest is non-native to said flax seed-specific promoter;

(b) introducing said chimeric nucleic acid construct into a flax plant cell; and (c) growing said flax plant cell into a mature flax plant capable of setting seed, wherein said nucleic acid sequence of interest is expressed in the seed under the control of said flax seed-specific promoter.

In a preferred embodiment of the invention, at least one expression characteristic, e.g. timing of expression in the plant's life cycle, conferred by the promoter to the non-native nucleic acid sequence is similar to that expression characteristic when conferred to a native nucleic acid sequence. In further preferred embodiments, the flax seed-specific promoter is an oleosin promoter, a 2S storage protein promoter or a legumin-like seed storage protein promoter.

In a further aspect, the present invention provides transgenic flax seeds prepared according to a method comprising:

(a) preparing a chimeric nucleic acid construct comprising in the 5' to 3' direction of transcription as operably linked components:
(1) a seed-specific promoter obtained from flax; and
(2) a nucleic acid sequence of interest wherein said nucleic acid of interest is non-native to said seed-specific promoter;

(b) introducing said chimeric, nucleic acid construct into a flax plant cell; and (c) growing said flax plant cell into a mature flax plant capable of setting seed, wherein said nucleic acid sequence of interest is expressed in the seed under the control of said seed-specific promoter.

In a further aspect the present invention provides flax plants capable of setting seed prepared by a method comprising:

(a) preparing a chimeric nucleic acid construct comprising in the 5' to 3' direction of transcription as operably linked components:
(1) a seed-specific promoter obtained from flax; and
(2) a nucleic acid sequence of interest wherein said nucleic acid of interest is non-native to said seed-specific promoter;

(b) introducing said chimeric nucleic acid construct into a flax plant cell; and (c) growing said flax plant cell into a mature flax plant capable of setting seed, wherein said nucleic acid sequence of interest is expressed in the seed under the control of said seed-specific promoter.

In yet a further aspect, the present invention provides novel flax seed specific promoters useful for the expression of non-native genes in flax seeds and the seeds of other plant species, useful for example for modification of the protein or oil composition of the seed.

In a preferred embodiment, the seed specific promoter comprises:

(a) a nucleic acid sequence as shown in FIG. 1 (SEQ.ID.NO.:1), FIG. 2 (SEQ.ID.NO.:4), FIG. 3 (SEQ.ID.NO.:6) or FIG. 4 (SEQ.ID.NO.:8) wherein T can also be U;

(b) a nucleic acid sequence that is complimentary to a nucleic acid sequence of (a);

(c) a nucleic acid sequence that has substantial sequence homology to a nucleic acid sequence of (a) or (b);

(d) a nucleic acid sequence that is an analog of a nucleic acid sequence of (a), (b) or (c); or (e) a nucleic acid sequence that hybridizes to a nucleic acid sequence of (a), (b), (c) or (d) under stringent hybridization conditions.

In another aspect, the invention provides chimeric nucleic acid sequences comprising a first nucleic acid sequence obtained from flax operatively linked to a second nucleic acid sequence non-native to said first nucleic acid sequence wherein said first nucleic acid sequence comprises a novel flax seed-specific promoter.

Other features and advantages of the present invention will become readily apparent from the following detailed description. It should be understood, however, that the detailed description and the specific examples while indicating preferred embodiments of the invention are given by way of illustration only, since various changes and modifications within the spirit and scope of the invention will become apparent to those skilled in the art of this detailed description.

BRIEF DESCRIPTION OF THE DRAWINGS

The invention will now be described in relation to the drawings in which:

FIGS. 1A–D show the DNA sequence (SEQ.ID.NO.:1) of a flax genomic clone encoding a 16.0 kDa oleosin protein (SEQ.ID.NOS.:2 and 3).

FIGS. 2A–C show the DNA sequence (SEQ.ID.NO.:4) of a flax genomic clone encoding a 18.6 kDa oleosin protein (SEQ.ID.NO.:5).

FIGS. 3A–B show the DNA sequence (SEQ.ID.NO.:6) of a flax genomic clone encoding a 2S storage protein (SEQ.ID.NO.:7).

FIGS. 4A–E show the DNA sequence (SEQ.ID.NO.:8) of a flax genomic clone encoding a 54.5 kDa legumin-like storage protein (SEQ.ID.NOS.:9–12).

FIGS. 9A–D show GUS expression in developing flax embryos and Arabidopsis seeds of plants transformed with a 2S protein gene promoter GUS fusion.

DETAILED DESCRIPTION OF THE INVENTION

Figure 5:
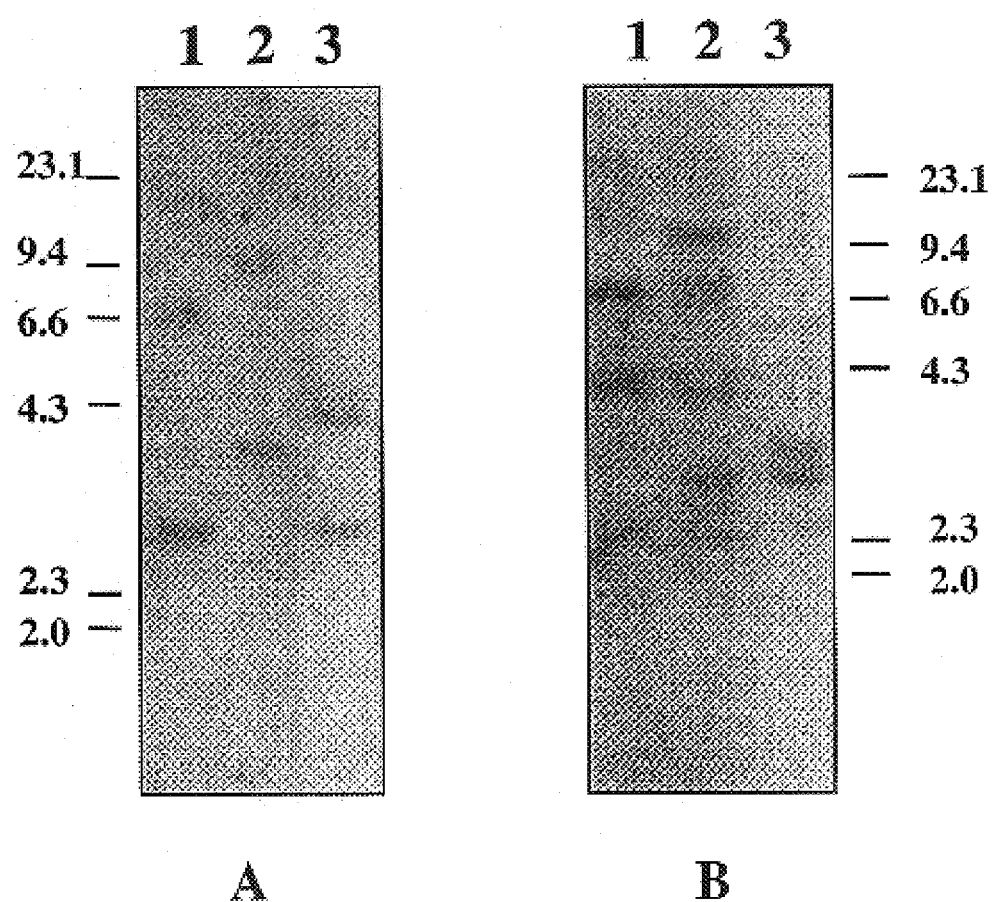
FIG. 5 shows Southern blot analysis of flax genomic DNA probed with flax oleosin DNA sequences.

As hereinbefore mentioned, the present invention relates to improved methods for the expression of non-native genes in plants, in particular flax. The invention provides methods allowing the seed-specific expression of non-native genes in flax. The methods of the invention are advantageous in that improved control over the expression of non-native genes in flax seeds is obtained. Expression of the non-native gene is restricted to the seeds, thereby limiting potential undesirable effects resulting from the expression in other plant organs or tissues. In addition, the provided methodology allows improved control over expression characteristics, such as the expression level of the non-native gene and timing of expression of the non-native gene in the developmental cycle of the plant. The methods of the present invention are particularly useful in that in accordance with the present invention the seed composition with respect to valuable raw materials, such as oil, protein and polysaccharides, may be altered both qualitatively and quantitatively.

Accordingly, in one aspect, the invention provides a method for the expression of a nucleic acid sequence of interest in flax seeds comprising:

(a) preparing a chimeric nucleic acid construct comprising in the 5' to 3' direction of transcription as operably linked components;
  (1) a seed-specific promoter obtained from flax; and
  (2) the nucleic acid sequence of interest wherein said nucleic acid of interest is non-native to said flax seed-specific promoter;
(b) introducing said chimeric nucleic acid construct into a flax plant cell; and
(c) growing said flax plant cell into a mature plant capable of setting seed, wherein said nucleic acid sequence of interest is expressed in the seed under the control of said flax seed-specific promoter.

As used herein, the term "non-native" refers to any nucleic acid sequence, including any RNA or DNA sequence, which is not normally associated with the seed-specific promoter. This includes heterologous nucleic acid sequences which are obtained from a different plant species as the promoter as well as homologous nucleic acid sequences which are obtained from the same plant species as the promoter but are not associated with the promoter in the wild-type (non-transgenic) plant.

The non-native nucleic acid sequence when linked to a seed-specific promoter obtained from flax results in a chimeric construct. The chimeric construct is introduced into a flax plant cell to create a transgenic flax plant cell which results in a detectably different phenotype of the flax plant cell or flax plant grown from it when compared with a non-transgenic flax plant cell or flax plant grown from it. A contiguous nucleic acid sequence identical to the nucleic acid sequence of the chimeric construct is not present in the non-transformed flax plant cell or flax plant grown from it. In this respect, chimeric nucleic acid sequences include those sequences which contain a flax promoter linked to a nucleic acid sequence obtained from another plant species or a nucleic acid sequence from flax but normally not associated with that promoter. Chimeric nucleic acid sequences as used herein further include sequences comprising a flax promoter and a nucleic acid sequence that is normally linked to the promoter but additionally containing a non-native nucleic acid sequence. For example, if the promoter is a flax seed-specific oleosin promoter, sequences "non-native" to the flax oleosin promoter also include a sequence comprising a fusion between the flax oleosin gene naturally associated with the oleosin promoter, and a coding sequence of interest that is not naturally associated with the promoter. The term non-native is also meant to include a fusion gene as hereinabove which additionally includes a cleavage sequence separating the nucleic acid sequence that is normally linked to the promoter sequence and the gene encoding the protein of interest.

The term "nucleic acid sequence" refers to a sequence of nucleotide or nucleoside monomers consisting of naturally occurring bases, sugars and intersugar (backbone) linkages. The term also includes modified or substituted sequences comprising non-naturally occurring monomers or portions thereof, which function similarly. The nucleic acid sequences of the present invention may be ribonucleic (RNA) or deoxyribonucleic acids (DNA) and may contain naturally occurring bases including adenine, guanine, cytosine, thymidine and uracil. The sequences may also contain modified bases such as xanthine, hypoxanthine, 2-aminoadenine, 6-methyl, 2-propyl, and other alkyl adenines, 5-halo uracil, 5-halo cytosine, 6-aza uracil, 6-aza cytosine and 6-aza thymine, pseudo uracil, 4-thiouracil, 8-halo adenine, 8-amino adenine, 8-thiol adenine, 8-thioalkyl adenines, 8-hydroxyl adenine and other 8-substituted adenines, 8-halo guanines, 8-amino guanine, 8-thiol guanine, 8-thioalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

The terms "seed-specific promoter" or "seed-preferred promoter", both of which terms may be used interchangeably herein, mean that a gene expressed under the control of the promoter is predominantly expressed in plant seeds with no or no substantial expression, typically less than 5% of the overall expression level, in other plant tissues.

In a further aspect, the present invention provides novel flax seed specific promoters useful for the expression of non-native genes in flax seeds and the seeds of other plant species. The promoters may be used to modify for example the protein, oil or polysaccharide composition of the seeds. In a preferred embodiment, the seed specific promoter comprises:

(a) a nucleic acid sequence as shown in FIG. 1 (SEQ.ID.NO.:1), FIG. 2 (SEQ.ID.NO.:4), FIG. 3 (SEQ.ID.NO.N:6) or FIG. 4 (SEQ.ID.NO.:8) wherein T can also be U;
(b) a nucleic acid sequence that is complimentary to a nucleic acid sequence of (a);
(c) a nucleic acid sequence that has substantial sequence homology to a nucleic acid sequence of (a) or (b);
(d) a nucleic acid sequence that is an analog of a nucleic acid sequence of (a), (b) or (c); or
(e) a nucleic acid sequence that hybridizes to a nucleic acid sequence of (a), (b), (c) or (d) under stringent hybridization conditions.

The term "sequence that has substantial sequence homology" means those nucleic acid sequences which have slight or inconsequential sequence variations from the sequences in (a) or (b), i.e., the sequences function in substantially the same manner and are capable of driving seed specific expression of non-native nucleic acid sequences. The variations may be attributable to local mutations or structural modifications. Nucleic acid sequences having substantial homology include nucleic acid sequences having at least 65%, more preferably at least 85%, and most preferably 90–95% identity with the nucleic acid sequences as shown in FIG. 1 (SEQ.ID.NO.:1), FIG. 2 (SEQ.ID.NO.:4), FIG. 3 (SEQ.ID.NO.:6) or FIG. 4 (SEQ.ID.NO.:8).

The term "sequence that hybridizes" means a nucleic acid sequence that can hybridize to a sequence of (a), (b), (c) or (d) under stringent hybridization conditions. Appropriate "stringent hybridization conditions" which promote DNA hybridization are known to those skilled in the art, or may be found in Current Protocols in Molecular Biology, John Wiley & Sons, N.Y. (1989), 6.3.1–6.3.6. For example, the following may be employed: 6.0×sodium chloride/sodium citrate (SSC) at about 45° C., followed by a wash of 2.0×SSC at 50° C. The stringency may be selected based on the conditions used in the wash step. For example, the salt concentration in the wash step can be selected from a high stringency of about 0.2×SSC at 50° C. In addition, the temperature in the wash step can be at high stringency conditions, at about 65° C.

The term "a nucleic acid sequence which is an analog" means a nucleic acid sequence which has been modified as compared to the sequence of (a), (b) or (c) wherein the modification does not alter the utility of the sequence (i.e. as a seed specific promoter) as described herein. The modified sequence or analog may have improved properties over the sequence shown in (a), (b) or (c). One example of a modification to prepare an analog is to replace one of the naturally occurring bases (i.e. adenine, guanine, cytosine or thymidine) of the sequence shown in FIG. 1, FIG. 2, FIG. 3 or FIG. 4 with a modified base such as such as xanthine, hypoxanthine, 2-aminoadenine, 6-methyl, 2-propyl and other alkyl adenines, 5halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecule shown in FIG. 1, FIG. 2, FIG. 3 or FIG. 4. For example, the nucleic acid sequences may contain phosphorothioates, phosphotriesters, methyl phosphonates, and phosphorodithioates.

A further example of an analog of a nucleic acid molecule of the invention is a peptide nucleic acid (PNA) wherein the deoxyribose (or ribose) phosphate backbone in the DNA (or RNA), is replaced with a polyamide backbone which is similar to that found in peptides (P.E. Nielsen, et al Science 1991, 254, 1497). PNA analogs have been shown to be resistant to degradation by enzymes and to have extended, lives in vivo and in vitro. PNAs also bind stronger to a complimentary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence.

In another aspect, the invention provides chimeric nucleic acid sequences comprising a first nucleic acid sequence obtained from flax operatively linked to a second nucleic acid sequence non-native to said first nucleic acid sequence wherein said first nucleic acid sequence comprises a novel flax seed-specific promoter. Preferably, the promoter is selected from the group of promoters comprising FIG. 1, FIG. 2, FIG. 3 and FIG. 4 or a nucleic acid sequence hybridizing thereto under stringent conditions.

In accordance with the present invention, the chimeric nucleic acid sequences can be incorporated in a known manner in a recombinant expression vector which ensures good expression in the seed cell. Accordingly, the present invention includes a recombinant expression vector comprising a chimeric nucleic acid sequence of the present invention suitable for expression in a seed cell.

The term "suitable for expression in a seed cell" means that the recombinant expression vectors contain the chimeric nucleic acids sequence of the invention, a regulatory region and a termination region, selected on the basis of the seed cell to be used for expression, which is operatively linked to the nucleic acid sequence encoding the polypeptide of desirable amino acid composition. Operatively linked is intended to mean that the chimeric nucleic acid sequence encoding the polypeptide is linked to a regulatory sequence and termination region which allows expression in the seed cell. A typical construct consists, in the 5' to 3' direction of a regulatory region complete with a promoter capable of directing expression in a plant, a polypeptide coding region and a transcription termination region functional in plant cells. These constructs may be prepared in accordance with methodology well known to those of skill in the art of molecular biology (see for example: Sambrook et al. (1990), Molecular Cloning, 2nd ed. Cold Spring Harbor Press). The preparation of constructs may involve techniques such as restriction digestion, ligation, gel electrophoresis, DNA sequencing and PCR. A wide variety of cloning vectors is available to perform the necessary cloning steps. Especially suitable for this purpose are the cloning vectors with a replication system that is functional in *Escherichia coli* such as pBR322, the pUC series M13mp series, pACYC184, pBluescript etc. Nucleic acid sequences may be introduced into these vectors and the vectors may be used to transform *E. coli* which may be grown in an appropriate medium. Plasmids may be recovered from the cells upon harvesting and lysing the cells. Final constructs may be introduced into plant vectors compatible with integration into the plant such as the Ti and Ri plasmids.

The methods for the expression of non-native genes in flax seeds in accordance with the present invention may be practiced using any flax seed-specific promoter and are not limited by the specific flax seed specific promoter that is selected. In preferred embodiments if the present invention, the flax seed-specific promoter confers to the non-native nucleic acid sequence at least one expression characteristic which is similar or identical to an expression characteristic conferred to the native nucleic acid sequence by the native promoter. The term "expression characteristic" as used herein refers to any measurable property or effect conferred by the flax seed-specific promoter to the nucleic acid sequence operably linked to the flax seed-specific promoter. Thus in preferred embodiments, timing of expression in the plant's life cycle, of the non-native nucleic acid sequence is similar or identical to timing of expression of the native nucleic acid sequence. In furthfer preferred embodiments, the expression level of the heterologous nucleic acid sequence is similar or identical to the expression level of the native nucleic acid sequence. In yet further specific embodiments, the response of the non-native gene to alterations in lighting conditions, changes in wavelength or light intensity for example, changes in temperature, tissue wounding, changes in concentration of chemical agents such as for example phytohormones and pesticides, is similar to the response of the native nucleic acid sequence to these stimuli. Other desired expression characteristics conferred by a flax seed-specific promoter may be recognized by those skilled in the art and a flax seed-specific promoter may be selected accordingly.

Flax-seed specific promoters that may be used in accordance with the present invention include promoters associated with seed storage proteins, such as all albumins and globulins, including the vicilin and legumin-like proteins, as well as seed-specific promoters not associated with seed storage proteins, such as oleosins. Of further particular interest are promoters associated with fatty acid metabolism, such as acyl carrier protein (ACP), saturases, desaturases, elongases and the like.

In preferred embodiments of the present invention the seed specific promoter used is an oleosin promoter, a legumin-like seed storage protein promoter or a 2S storage protein promoter. In particularly preferred embodiments the seed specific promoter has the sequence shown in FIG. 1, FIG. 2, FIG. 3 or FIG. 4 or any nucleic acid sequences obtainable from flax and hybridizing to any one of these four nucleic acid sequences under stringent conditions.

Additional flax seed-specific promoters may be used in accordance with the present invention. These promoters may be obtained in a number of ways. Where a flax seed protein has been isolated, it may be partially sequenced, so that a nucleic acid probe may be designed for identifying RNA specific to the seed. To further enhance the RNA specifically associated with the seed, cDNA may be prepared from seed cells and the cDNA may be subtracted with mRNA or cDNA from non-seed cells. The remaining seed cDNA may then be used to probe a genomic DNA library for complementary sequences. Sequences hybridizing to the cDNA may subsequently be obtained and the associated promoter region may be isolated. It is also possible to screen genomic DNA libraries prepared from flax seed tissues using known seed specific genes from other plant species and subsequently isolate their associated promoters. Due to the relative abundance of seed-storage proteins in seeds it is also be possible to obtain sequence information through random sequencing of flax seed cDNA libraries. Those cDNA sequences matching sequence of known seed-storage proteins could be used to identify the associated promoter. Databases containing sequence information from large scale sequencing from for example Arabidopsis and maize may be searched for known seed-specific proteins and/or promoters and the information may be used to identify promoter sequences in flax that share sequence similarity. Alternative methods to isolate additional flax seed specific promoters may be used and novel flax seed specific promoters may be discovered by those skilled in the art and used in accordance with the present invention.

The nucleic acid sequence of interest linked to the promoter may be any nucleic acid sequence of interest including any RNA or DNA sequence encoding a peptide or protein of interest, for example, an enzyme, or a sequence complementary to a genomic sequence, where the genornic sequence may be at least one of an open reading frame, an intron, a non-coding leader sequence, or any sequence where the complementary sequence will inhibit transcription, messenger RNA processing, for example splicing or translation. The nucleic acid sequence of interest may be synthetic, naturally derived or a combination thereof. As well, the nucleic acid sequence of interest could be a fragment of the natural sequence, for example just include the catalytic domain or a structure of particular importance. Depending upon the nature of the nucleic acid sequence of interest, it may be desirable to synthesize the sequence with plant preferred codons. The plant preferred codons may be determined from the codons of highest frequency in the proteins expressed in the largest amount in particular plant species of interest.

The nucleic acid sequence of interest may encode any of a variety of recombinant proteins. Examples of recombinant proteins which might be expressed by the methods of the present invention include proteins with a favorable catalytic function or a valuable protein that will accumulate to high levels and be extracted if desired. Proteins with a catalytic function, include, but are not limited to, proteins that confer a new biochemical phenotype on the developing seeds. New phenotypes could include such modifications as altered seed-protein or seed oil composition or seed polysaccharide composition, enhanced production of pre-existing desirable products or properties and the reduction or even suppression on an undesirable gene product using antisense, ribozyme or co-supression technologies (Izant and Weintraub (1984) Cell 26: 1007–1015, antisense; Hazelhoff and Gerlach (1988) Nature 334: 585–591, ribozyme; Napoli et al. (1990) Plant Cell 2: 279–289, co-suppression).

It is expected that the desired proteins would be expressed in all embryonic tissues, although varying cellular expression may be detected in the different embryonic tissues such as the embryonic axis and cotyledons. The nucleic acid sequence of interest may be expressed at any stage in seed development. The timing of expression may depend on the particular use of the invention. Expression of enzymes involved in oil modification may be desirable early in seed development, for example before accumulation of seed storage protein.

Besides the promoter region and the nucleic acid sequence of interest, a nucleic acid sequence capable of terminating transcription is typically included in expression vectors. Transcriptional terminators are preferably about 200 to about 1,000 nucleotide base pairs and may comprise any such sequences functional in plants, such as the nopaline synthase termination region (Bevan et al., (1983) Nucl. Acid. Res. 11: 369–385), the phaseolin terminator (van der Geest et al., (1994) Plant J. 6(3): 413–423), the terminator for the octopine synthase gene of *Agrobacterium tumefaciens* or other similarly functioning elements. These transcription terminator regions can be obtained as described by An (1987), Methods ii Enzym. 153: 292 or are already present in plasmids available from commercial sources such as ClonTech, Palo Alto, Calif. The choice of the appropriate terminator may have an effect of the rate of transcription.

The chimeric construct may further comprise enhancers such as the AMV leader (Jobling and Gehrke (1987), Nature 325: 622–625) or introns. It should be understood that the design of the expression vector may depend on such factors as the choice of the plant species and/or the type of polypeptide to be expressed.

The expression vectors will normally also contain a marker gene. Marker genes comprise all genes that enable distinction of transformed plant cells from non-transformed cells, including selectable and screenable marker genes. Conveniently, a marker may be a resistance marker to a herbicide, for example, glyphosate or phosphinothricin, or to an antibiotic such as kanamycin, G418, bleomycin, hygromycin, chloramphenicol and the like, which confer a trait that can be selected for by chemical means. Screenable markers may be employed to identify transformants through observation. They include but are not limited to the β-glucuronidase or uidA gene, a β-lactamase gene or a green fluorescent protein (Niedz et al. (1995) Plant Cell Rep. 14: 403).

In order to introduce nucleic acid sequences into plant cells in general a variety of techniques are available to the skilled artisan. Agrobacterium-mediated transformation for flax plant cells has been reported and flax transformants may be obtained in accordance with the methods taught by Dong and McHughen (1993) Plant Science 88: 61–77, although a variety of other techniques (see below) may also be used to introduce the chimeric DNA constructs in flax cells if so desired.

Transformed flax plants grown in accordance, with conventional agricultural practices known to a person skilled in the art are allowed to set seed. Flax seed may then be obtained from mature flax plants and analyzed for desired altered properties with respect to the wild-type seed.

Two or more generations of plants may be grown and either crossed or selfed to allow identification of plants and strains with desired phenotypic characteristics including production of the recombinant polypeptide. It may be desirable to ensure homozygosity in the plants to assure continued inheritance of the recombinant trait. Methods for selecting homozygous plants are well known to those skilled in the art of plant breeding and include recurrent selfing and selection and anther and microspore culture. Homozygous plants may also be obtained by transformation of haploid cells or tissues followed by regeneration of haploid plantlets subsequently converted to diploid plants by any number of known means (e.g. treatment with colchicine or other microtubule disrupting agents).

The present invention also includes transgenic flax seeds prepared according to a method comprising:
  (a) preparing a chimeric nucleic acid construct comprising in the 5' to 3' direction of transcription as operably linked components:
    (1) a seed-specific promoter obtained from flax; and
    (2) a nucleic acid sequence of interest wherein said nucleic acid of interest is non-native to said seed-specific promoter;
  (b) introducing said chimeric nucleic acid construct into a flax plant cell; and
  (c) growing said flax plant cell into a mature flax plant capable of setting seed
  wherein said nucleic acid sequence of interest is expressed in the seed under the control of said seed-specific promoter.

In preferred embodiments of the invention the seed-specific promoter is selected from the group of flax seed specific promoters consisting of, a 2S storage protein promoter, a globulin promoter, an oleosin promoter, and a legumin-like seed storage protein promoter. Specific promoter sequences are shown in FIG. 1 (SEQ.ID.NO.:1), FIG. 2 (SEQ.ID.NO.:4), FIG. 3 (SEQ.ID.NO.:6) and FIG. 4 (SEQ.ID.NO.:8).

The present invention further provides flax plants capable of setting seed prepared by a method comprising:
  (a) preparing a chimeric nucleic acid construct comprising in the 5' to 3' direction of transcription as operably linked components:
    (1) a seed-specific promoter obtained from flax; and
    (2) a nucleic acid sequence of interest wherein said nucleic acid of interest is non-native to said seed-specific promoter;
  (b) introducing said chimeric nucleic acid construct into a flax plant cell; and
  (c) growing said flax plant cell into a mature flax plant capable of setting seed
  wherein said nucleic acid sequence of interest is expressed in the seed under the control of said seed-specific promoter.

The present invention further provides methods of use for the novel promoters shown in FIG. 1 (SEQ.ID.NO.:1), FIG. 2 (SEQ.ID.NO.:4), FIG. 3 (SEQ.ID.NO.:6) and FIG. 4 (SEQ.ID.NO.:8) in plant species other than flax. Accordingly, the invention also includes the preparation of chimeric nucleic acid constructs comprising a promoter selected from the group promoters shown in FIG. 1, FIG. 2, FIG. 3 and FIG. 4 and a nucleic acid sequence of interest, and expression in a seed-specific manner of the nucleic acid sequence of interest in plant species other than flax and under the control of the flax promoter.

In another aspect of the present invention there is provided a method for the expression of a nucleic acid sequence of interest in plant seeds comprising:
  (a) preparing a chimeric nucleic acid construct comprising in the 5' to 3' direction of transcription as operably linked components;
    (1) a seed-specific promoter selected from the group of seed-specific promoters consisting of
      (i) a nucleic acid sequence as shown in FIG. 1 (SEQ.ID.NO.:1), FIG. 2 (SEQ.ID.NO4), FIG. 3 (SEQ.ID.NO.:6) or FIG. 4 (SEQ.ID.NO.:8) wherein T can also be U;
      (ii) a nucleic acid sequence that is complimentary to a nucleic acid sequence of (i);
      (iii) a nucleic acid sequence that has substantial sequence homology to a nucleic acid sequence of (i) or (ii); and
      (iv) a nucleic acid sequence that is an analog of a nucleic acid sequence of (i), (ii) or (iii);
      (v) a nucleic acid sequence that hybridizes to a nucleic acid sequence of (i), (ii), (iii) or (iv) under stringent hybridization conditions; and
    (2) said nucleic acid of interest;
  (b) introducing the chimeric nucleic acid construct into a plant cell;
  (c) growing said plant cell into a mature plant capable of setting seed, wherein said nucleic acid sequence of interest is expressed in the seed under the control of said seed-specific promoter.

A variety of techniques are available for the introduction of nucleic acid sequences, in particular DNA, into plant host cells in general. For example, the chimeric DNA constructs may be introduced into host cells obtained from dicotelydenous plants, such as tobacco, and oleoagenous species, such as *Brassica napus* using standard Agrobacterium vectors by a transformation protocol such as described by Moloney et al. (1989), Plant Cell Rep. 8: 238–242 or Hinchee et al. (1988) Bio/Technol. 6: 915–922; or other techniques known to those skilled in the art. For example, the use of T-DNA for transformation of plant cells has received extensive study and is amply described in EP 0 120 516, Hoekema et al., (1985), Chapter V In: *The Binary Plant Vector System* Offset-drukkerij Kanters BV, Alblasserdam); Knauf et al. (1983), *Genetic Analysis of Host Expression by Agrobacterium*, p. 245, In: *Molecular Genetics of Bacteria-Plant Interaction*, Puhler, A. ed. Springer-Verlag, N.Y.); and An et al., (1985), (EMBO J., 4: 277–284). Agrobacterium transformation may also be used to transform monocot plant species (U.S. Pat. No. 5,591,616).

Conveniently, explants may be cultivated with *Agrobacterium tumefaciens* or *Agrobacterium rhizogenes* to allow for the transfer of the transcription construct in the plant host cell. Following transformation using Agrobacterium the plant cells are dispersed into an appropriate medium for selection, subsequently callus, shoots and eventually plants are recovered. The Agrobacterium host will harbour a plasmid comprising the vir genes necessary for transfer of the T-DNA to plant cells. For injection and electroporation (see below) disarmed Ti-plasmids (lacking the tumour genes, particularly the T-DNA region) may be introduced into the plant cell.

The use of non-Agrobacterium techniques permitis the use of constructs described herein to obtain transformation and expression in a wide variety of monocotyledonous and dicotyledonous plant species. These techniques are especially useful for transformation of plant species that are intractable in an Agrobacterium transformation system. Other techniques for gene transfer include particle bombardment (Sanford, (1988), Trends in Biotechn. 6: 299–302), electroporation (Fromm et al., (1985), PNAS USA, 82: 5824–5828; Riggs and Bates, (1986), PNAS USA 83: 5602–5606), PEG mediated DNA uptake (Potrykus et al., (1985), Mol. Gen. Genetics., 199: 169–177), microinjection (Reich et al., Bio/Techn. (1986) 4:1001–1004) and silicone carbide whiskers (Kaeppler et al. (1990) Plant Cell Rep. 9: 415–418).

In a further specific applications such as to *B. napus*, the host cells targeted to receive recombinant DNA constructs typically will be derived from cotyledonary petioles as described by Moloney et al. (1989) Plant Cell Rep. 8: 238–242. Other examples using commercial oil seeds include cotyledon transformation in soybean explants (Hinchee et al., (1988) Bio/Technol. 6: 915–922) and stem transformation of cotton (Umbeck et al., (1987) Bio/Technol. 5: 263–266).

Following transformation, the cells, for example as leaf discs, are grown in selective medium. Once the shoots begin to emerge, they are excised and placed onto rooting medium. After sufficient roots have formed, the plants are transferred to soil. Putative transformed plants are then tested for presence of a marker. Southern blotting is performed on genomic DNA using an appropriate probe, to show integration into the genome of the host cell.

The methods provided by the present invention can be used in conjunction a broad range of plant species. Particularly preferred plant cells employed in accordance with the present invention include cells from the following plants: soybean (*Glycine max*), rapeseed (*Brassica napus, Brassica campestris*), sunflower (*Helianthus annuus*), cotton (*Gossypium hirsutum*), corn (*Zea mays*), tobacco (*Nicotiana tobacum*), alfalfa (*Medicago sativa*), wheat (Triticum sp.), barley (*Hordeum vulgare*), oats (*Avena sativa* L.), sorghum (*Sorghum bicolor*), *Arabidopsis thaliana*, potato (Solanum sp.), flax/linseed (*Linum usitatissimum*), safflower (*Carthamus tinctorius*), oil palm (*Eleais guineeis*), groundnut (*Arachis hypogaea*), Brazil nut (*Bertholletia excelsa*) coconut (*Cocus nucifera*), castor (*Ricinus communis*), coriander (*Coriandrum sativum*), squash (*Cucurbita maxima*), jojoba (*Simmondsia chinensis*) and rice (*Oryza sativa*).

The present invention has a variety of uses which include improving the intrinsic value of plant seeds by their accumulation of altered polypeptides or novel recombinant peptides or by the incorporation or elimination or a metabolic step. Use of the invention may result in improved protein quality (for example, increased concentrations or essential or rare amino acids), improved liquid quality by a modification of fatty acid composition, or improved or elevated carbohydrate composition. Examples include the expression of sulfur-rich proteins, such as those found in lupins or brazil nuts in a seed deficient in sulphurous amino acids. Improved protein quality could also be achieved by the expression of a protein or a fragment of a protein that is enriched in essential amino acids including lysine, cysteine, methionine and tryptophan. Alternatively, a fatty acyl coenzyme A, a transferase enzyme capable of modifying fatty acid ratios in triglycerides (storage lipid) could be expressed. In cases where a recombinant protein is allowed to accumulate in the seed, the protein could also be a peptide which has pharmaceutical or industrial value. In this case the peptide could be extracted from the seed and used in crude or purified form as appropriate for the intended use. As well, the polypeptides that are expressed in the seeds can be fragments or derivatives or the native protein. Pharmaceutically useful proteins may include, but are not limited to, anticoagulants, such as hirudin, antibodies, including monoclonal antibodies and antibody fragments, vaccines, cytokines or growth factors such as bovine growth factor, cholinergic differentiation factor (CDF), ciliary neurotrophic factor (CNTF), fibroblast growth factor (FGF), fish growth factor, gonadotropin, granulocyte-colony stimulating factor (G-CSF), granulocyte-macrophage colony-stimulating factor (GM-CSF), human growth hormone, interferon alpha (IFN-$\alpha$), interferon beta (IFN-$\beta$), interferon gamma (IFN-$\gamma$), interleukin 1-alpha (IL1-$\alpha$), interleukin 1-beta (IL1-$\beta$), interleukin-2 (IL-2), interleukin-3 (IL-3), interleukin-4 (IL-4), interleukin-5 (IL-5), interleukin-6 (IL-6), interleukin-10 (IL-10), leukemia inhibitory factor (LIF), thioredoxin, macrophage colony-stimulating factor (M-CSF), myelomonocytic growth factor, nerve growth factor (NGF), oncostatin M, platelet-derived growth factor (PDGF), prolactin, transforming growth factor alpha (TGF-$\alpha$), transforming growth factor beta2 (TGF-$\beta$2), tumour necrosis factor alpha (TNF-$\alpha$), and tumour necrosis factor beta (TNF-$\beta$). Pharmaceutically useful proteins can also include mammalian proteins, for example, but not limited to $\alpha$-1-antitrypsin, anti-obesity proteins, blood proteins, collagen, collagenase, elastin, elastase, enteropeptidase, fibrinogen, haemoglobin, human serum albumin, insulin, lactoferrin, myoglobin and pulmonary surfactant proteins.

Industrially useful peptides may include, but are not limited to $\alpha$-amylase or other amylases, amyloglucosidase, arabinase, catalase, cellobiohydrolase, cellulases, chitinases, chymotrypsin, dehydrogenases, endo-glucanase, chymosin, endo-galactanase, esterases, $\beta$-galactosidase, $\alpha$-galactosidase or other galactosidases, gastric lipases, glucanases, glucose isomerase, hemi-cellulases, hydrolases, isomerase, ligninases, lipases, lyases, lysozymes, oxidases, oxidoreductase, papain, pectinases, pectin lyase, peroxidases, phosphatases, phytase, proteases, pullulanases, reductases, serine proteases, thioredoxin, transferase, trypsin, and xylanase.

The following non-limiting examples are illustrative of the present invention:

EXAMPLES

Example 1

Isolation of Seed-Specific Flax Promoters

Seed specific cDNA clones were isolated form a flax seed specific cDNA-library. These cDNA clones were sequenced and the Basic Local Alignment Search Tool (BLAST) was used to compare these sequences against others in public databases such as Genbank. This comparison revealed that the deduced amino acid sequence of several of the isolated cDNAs had a high degree of similarity to both the low and high molecular weight class of oleosins, 2S-albumin and legumin-like storage proteins. Probes were prepared individually from (portions of) cDNAs encoding oleosins, 2S albumin and legumin-like storage proteins and these were used to screen a genomic library prepared from the flax line Forge that is homozygous for four rust resistance genes (Anderson et al. (1997), The Plant Cell 9: 641–651). Several positive lambda clones for each probe were identified after high-stringency screening. The inserts were subcloned into the plasmid vector pBluescript and sequenced. Sequence information revealed that we had isolated the genomic counterparts to the oleosins, 2S albumin and cDNAs legumin-like cDNAs. Sequence information of the genomic clones containing sequences encoding a high and low molecular weight oleosin isoforms, 2S albumin and a legumin-like gene are presented in FIGS. 1 to 4 respectively.

FIG. 1 and SEQ.ID.NO.:1 shows the DNA sequence of a flax genomic clone encoding a 16.0 kDa oleosin protein (low molecular weight or L-isoform). Putative regulatory elements are identified and indicated. These include inverted repeats (base pairs 805 to 813 and 821 to 829; base pairs 1858 to 1866 and 1877 to 1885), direct repeats (base pairs 184 to 193 and 1102 and 1111; base pairs 393 to 402 and 1701 to 1710; base pairs 683 to 692 and 1546 to 1555; base pairs 770 to 781 and 799 to 810; base pairs 955 to 964 and 1936 to 1945; base pairs 1483 to 1496 and 1513 to 1526), the abscisic acid responsive element (ABRE) (base pairs 1859 to 1866), CACA box (base pairs 1933 to 1936), TATA box (base pairs 1925 to 1931) and CAT box (base pairs 1989 to 1993). As well, the poly adenylation signal is indicated (base pairs 3020 to 3025). The open reading frame is interrupted by 1 short intron (which are marked) and the 2 exons are translated and indicated in IUPAC single letter amino-acid codes.

FIG. 2 and SEQ.ID.NO.:4 shows the DNA sequence of a flax genomic clone encoding a 18.6 kDa oleosin protein (high molecular weight or H-isoform). Putative regulatory elements are identified and indicated. These include direct repeats (base pairs 14 to 25 and 1427 to 1438; base pairs 80 to 89 and 1242 to 1251; base pairs 177 to 186 and 837 to 846; base pairs 1281 to 1290 and 1242 to 1251; base pairs 1591 to 1600 and 1678 to 1287). The open reading frame is not interrupted by introns and is translated and indicated in IUPAC single letter amino-acid codes.

FIG. 3 and SEQ.ID.NO.:6 shows the DNA sequence of the flax genomic clone encoding a 2S storage protein. Nucleotide sequencing of this clone revealed it to have an open reading frame of 174 amino acids that showed homology to the plant 2S storage group of proteins. The sequence encodes an open reading frame with 38% overall similarity to a *Brassica oleracea* 2S storage protein, including complete conservation of the glutamine-rich stretch QQQGQQQGQQQ (SEQ.ID.NO.:13). In addition, the 2S storage protein gene promoter contained several putative promoter regulatory elements. These include AT rich repeats (base pairs 25–36, 97–108 and 167–190), RY-like repeat (base pairs 240–247), G-box-like element (base pairs 274–280), seed specific box-like motif (base pairs 285–290) and TATA box (base pairs 327–333).

FIG. 4 and SEQ.ID.NO.:8 shows the DNA sequence of a flax genomic clone encoding a 54.4 kDa flax legumin-like seed storage protein. This legumin-like seed storage protein gene will also be referred to as "linin". The deduced amino acid sequence of the linin gene was compared to the legumin-like protein from *R. communis*, the legumin precursor from *M. salicifolia, Q.robur* and *G. hirsutum*, the glutelin precursor from *O. sativa* and a 12 S seed storage protein from *A. thaliana*. The linin gene shows a sequence identity/similarity with the corresponding proteins from *R. communis, M. salicifolia, Q. robur, G. hirsutum, O. sativa* and *A. thaliana* of 59/15, 47/16, 50/17, 45/17, 43/18 and 43/18 percent respectively. Putative regulatory elements in the promoter region are identified and indicated. These include inverted repeats (base pairs 265 to 276 and 281 to 292; base pairs 513 to 524 and 535 to 545), repeats (base pairs 1349 to 1360 and 1367 to 1378; base pairs 1513 to 1529 and 1554 to 1572), the abscisic acid responsive element (ABRE) (base pairs 1223 and 1231), legumin box (RY repeats) (between base pairs 1223 and 1231), a possible vicilin box region (base pairs 1887 to 1894), CAAT box (base pairs 1782 to 1785) and TATA box (base pairs 1966 to 1970). As well, the signal peptide for ER membrane targeting is indicated (base pairs 2034–2080). The open reading frame is interrupted by 3 short introns (which are marked) and the 4 exons are translated and indicated in IUPAC single letter amino-acid codes.

FIG. 5 shows Southern blot analysis of flax genomic DNA. 60 μg of flax genomic DNA was isolated from leaves, digested with EcoRI (lane I), HindIII (lane 2) and BamHI (lane 3) and was loaded into the respective lanes. A) Hybridizations were performed with random primed $^{32}$P-labelled 3T cDNA (high molecular weight flax oleosin isoform). B) Hybridizations were performed with random primed $^{32}$P-labelled 7R cDNA (low molecular weight flax oleosin isoform). The results demonstrate that both 3T (high molecular weight oleosin isoform) and 7R (low molecular weight oleosin isoform) oleosin cDNAs hybridize with flax genomic DNA. More specifically the results indicate that 3T is likely to a 2-copy gene in flax, as seen by two bands in each lane of digestion. Similarly, 7R is likely to represent a multigene family in flax as multiple bands were detected for each digestion.

Example 2
Seed Specific Expression of Flax Oleosin Genes

Figure 6:
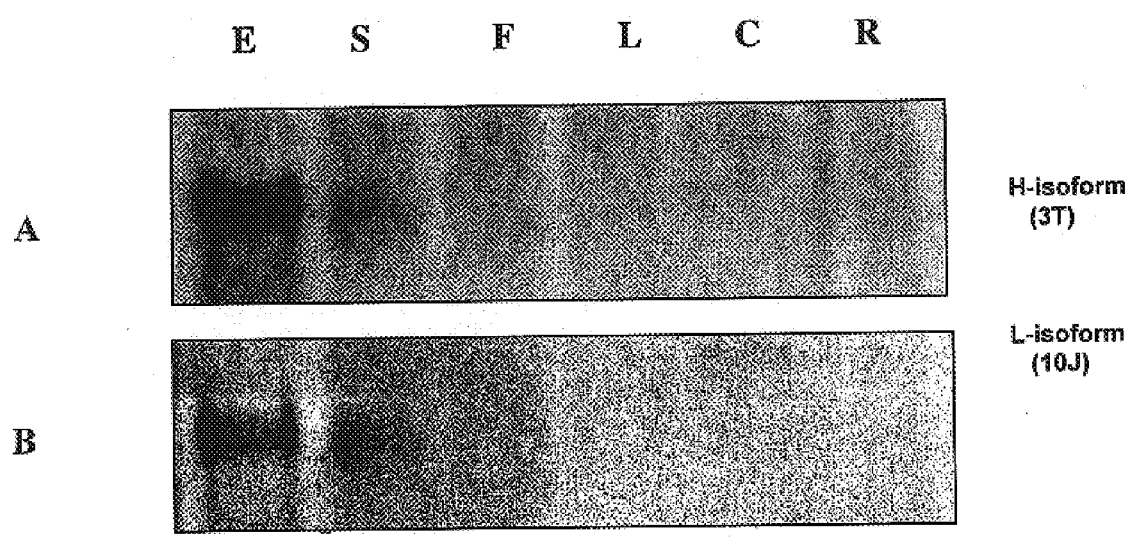
FIG. 6 shows a Northern blot analysis of the seed specific expression of flax oleosins.

FIG. 6 shows a Northern blot analysis of the seed specific expression of flax oleosins. Northern hybridization of the two oleosin mRNA in different tissues. Ten μg of total RNA was extracted from different tissues, R, root; C, cotyledon; L, leaf; S, seed capsule; E, embryo. The membrane was probed with (A) cDNA encoding high molecular weight (H)-isoform (identical to coding sequence as presented in FIG. 2) and (B) cDNA encoding low molecular weight (L)-isoform (identical to coding sequence as presented in FIG. 1). Both the transcripts are expressed only in the embryo and seed capsule, which contains embryos.

Figure 7:
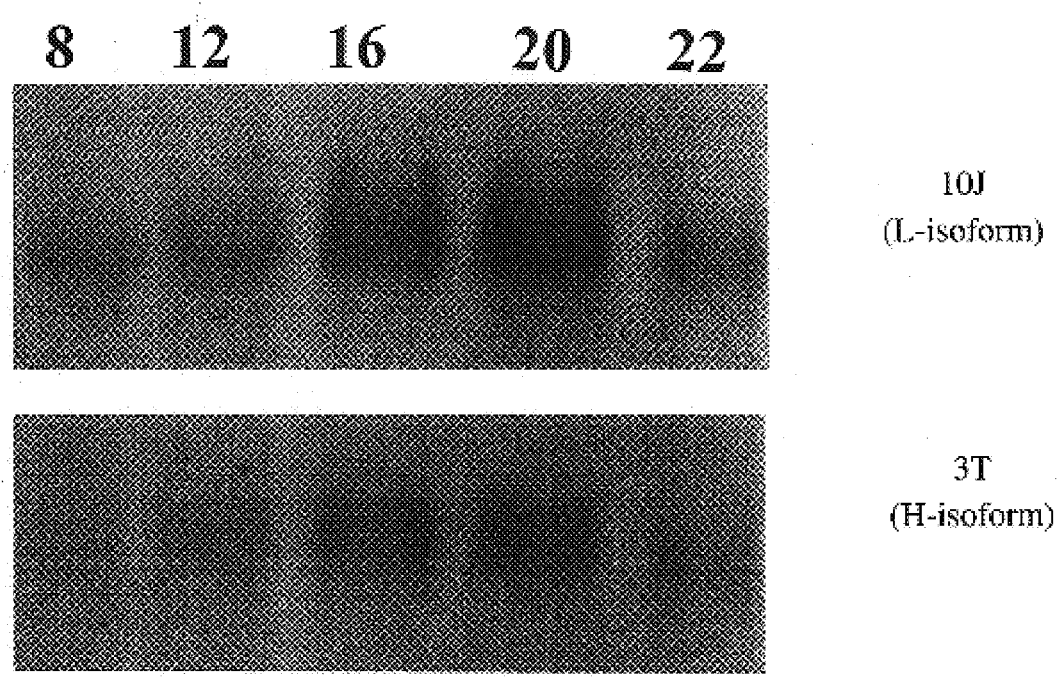
FIG. 7 shows a Northern blot analysis of the developmental expression of flax oleosins during seed development.

Example 3
Developmental Expression of Flax Oleosin Genes During Seed Development FIG. 7 shows a Northern blot analysis of the developmental expression of flax oleosins during seed development. 15 μg per lane of total RNA was loaded in each lane on agarose/formaldehyde gel and blotted onto HybondN+ membrane. 10J: This membrane was probed using the $^{32}$P dCTP labeled flax oleosin cDNA clone (low molecular weight isoform). Stages indicated are the number of days past anthesis (DPA). 3T) 15 μg per lane of total RNA was loaded in each lane on agarose/formaldehyde gel and blotted onto HybondN+ membrane. 3T: This membrane was probed using the $^{32}$P dCTP labeled flax oleosin cDNA clone (high molecular weight isoform). Both the transcripts were expressed very early in development (6DPA, early cotyledonary stage). Expression is maximum at 16 to 20 DPA (late cotyledonary stage) and declines at 22 DPA (mature embryos).

Example 4
Transient Seed Specific Expression of β-glucuronidase (GUS) When Under the Regulatory Control of Flax Oleosin Regulatory Sequences Two constructs were made using standard molecular biology techniques (eg see Sambrook et al. (1990), Molecular Cloning, 2nd ed. Cold Spring Harbor Press, including restriction enzyme digestions, ligation and polymerase chain reaction (PCR).

Construct pSC54: The β-glucuronidase reporter coding sequence from vector GUSN358>S (Clontech Laboratories) was placed between the promoter sequence from nucleotide 21 to 1852 and terminator sequence from 2395 to 3501 (as described in FIG. 1). This insert was cloned into pBluescript and the resulting vector is called pSC54.

Figure 8:
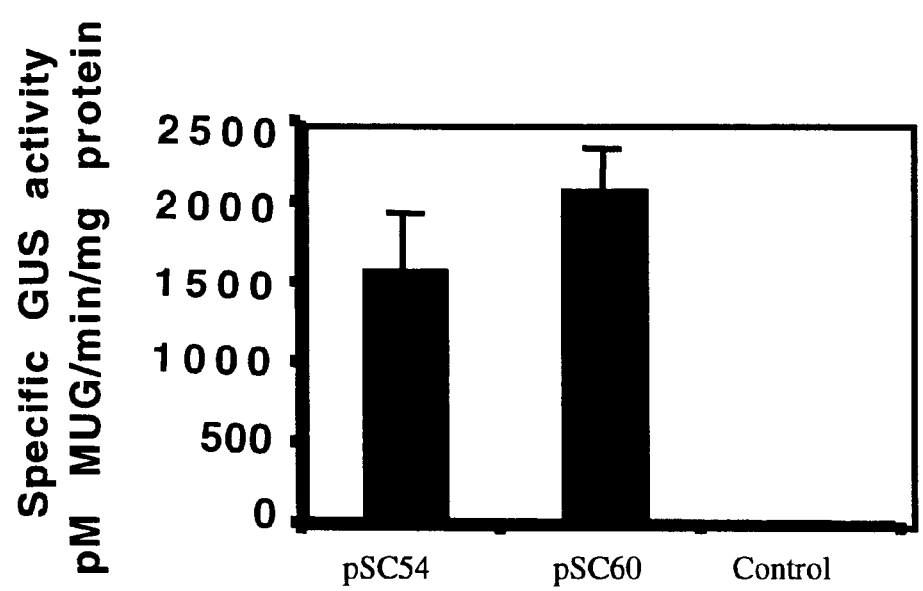
FIG. 8 shows the GUS activity of flax embryos bombarded with flax oleosin promoter-GUS-flax terminator gene constructs.

Construct pSC60: The β-glucuronidase reporter coding sequence from vector GUSN358>S (Clontech Laboratories) was placed between the promoter sequence from nucleotide 1 to 2023 and terminator sequence from 2867 to 3925 (as described in FIG. 2). This insert was cloned into pBluescript and the resulting vector is called pSC60.

pSC54, pSC60 and a promoter-less GUS construct (Control) were introduced into the flax embryos using particle bombardment using standard protocols (eg see Abenes et al. (1997) Plant Cell reports 17:1–7). FIG. 8 shows the GUS activity of flax embryos bombarded with pSC54, pSC60 and a promoterless GUS construct measured 48 hours after particle bombardment. As can be seen the flax oleosin regulatory sequences are sufficient to drive the expression of GUS in flax embryos.

Example 5
Stable Seed Specific Expression of β-glucuronidase (GUS) in Flax and Arabidopsis When Under the Regulatory Control of Flax 2S Storage Protein Gene Promoter A GUS reporter gene construct was made by incorporating 5' and 3' regions from the DNA fragment described in FIG. 3 into promoterless-GUS pBI101 vector as follows.

A 400 bp amplicon from the 5' end of the DNA fragment described in FIG. 3 was PCR amplified using the following primers (location shown in FIG. 3):

5' primer(1): 5'-TCCACTATGTAGGTCATA-3' (SEQ.ID.NO.:14)

3' primer(1): 5'-CTTTAAGGTGTGAGAGTC-3' (SEQ.ID.NO.:15)

The PCR primers also contained restriction sites for HindIII and BamHI which, were used to clone the 400 bp 5' UTR amplicon into the HindIII/BamHI sites of the pBI101 vector in front of the GUS reporter gene. A 736 bp amplicon from the 3' untranslated region (3'UTR) of the DNA fragment described in FIG. 3 was PCR amplified using the following primers (location shown in FIG. 3):

5' primer (2):5'-AGGGGTGATCGATTA-3' (SEQ.ID.NO.:16)

3' primer (2):5'-GATAGAACCCACACGAGC-3' (SEQ.ID.NO.:17)

The PCR primers also contained restriction sites for SacI and EcoRI. The NOS terminator region of the pBI101 vector was cut out with SacI/EcoRI digestion and replaced with the similarly digested: 736 bp 3'UTR amplicon of the DNA fragment described in FIG. 3.

The GUS reporter construct was then electroporated into *Agrobacterium tumifaciens* strain AGL1 and transformation of flax (Finnegan et al. (1993) Plant Mol Biol. 22(4): 625–633) and Arabidopsis (Valvekens et al. Proc. Natl. Acad. Sci. 85: 5536–5540) carried out according to previously described protocols.

Various tissues from flax and Arabidopsis plants carrying the GUS reporter construct were assayed histologically for evidence of GUS activity. In the case of flax, leaf tissue, root tissue and mid-maturity embryos dissected out of developing seeds were stained for GUS activity. For Arabidopsis, developing seeds were stained for GUS in situ in their siliques.

Figure 9D:
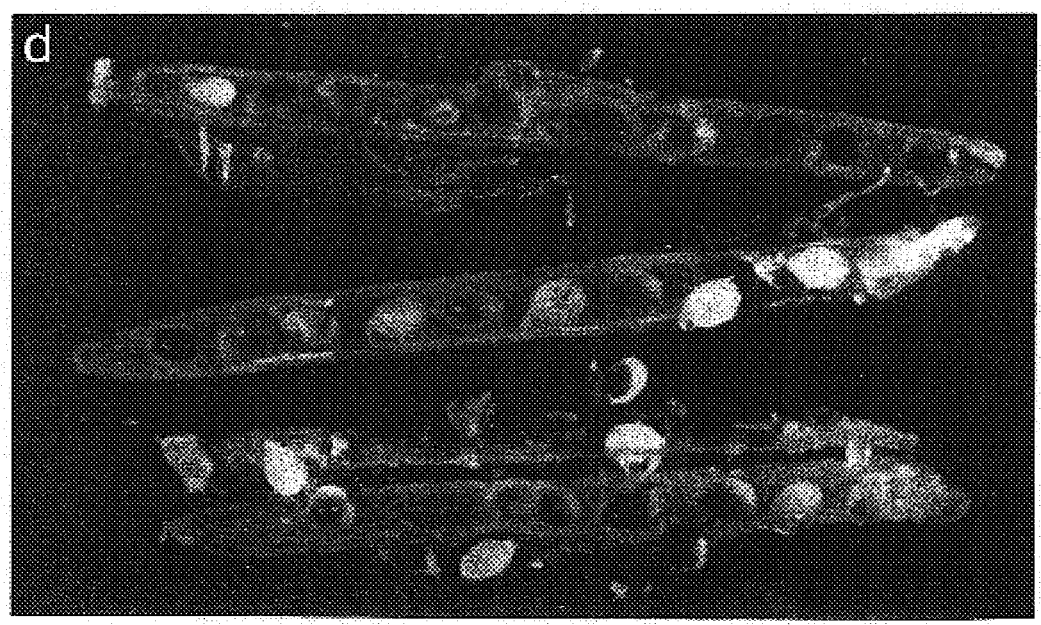

GUS staining was carried out by immersing the tissues in histochemical buffer containing 0.5 mM X-gluc, 0.5 M potassium phosphate buffer (pH 7.0), 1 mM EDTA, 0.5 M sorbital, 0.5 mM potassium ferricyanide and 0.5 mM potassium ferrocyanide. The staining reaction was carried out for 12–16 hrs at 37° C. and the reaction was stopped by adding 95% ethanol. Tissues were subsequently cleared of chlorophyll by repeated washing in 95% ethanol prior to photography. FIG. 9 shows clear evidence of strong GUS activity in developing flax embryos and Arabidopsis seeds, and no evidence of GUS reporter gene expression in flax roots or leaves, or in Arabidopsis silique walls.

Example 6
Stable Seed Specific Expression of β-glucuronidase (GUS) in Flax, Arabidopsis and *Brassica napus* When Under the Regulatory Control of Flax Legumin-like Storage Protein Gene Regulatory Sequences A construct was made using standard molecular biology techniques, including restriction enzyme digestions, ligation and polymerase chain reaction (PCR). In order to obtain a DNA fragment containing approximately 2 kilobases from the 5' transcriptional initiation region of the flax legumin-like seed storage protein in a configuration suitable for ligation to a GUS coding sequence, a PCR based approach was used. This involved the use of the polymerase chain reaction to amplify the precise sequence desired for the expression analysis. To perform the necessary PCR amplification, two oligonucleotide primers were synthesized (Beckman Oligo 1000 M DNA synthesizer) have the following sequences:

5' primer: 5'T*ATCTAGA*CTCAAGCATACGGACAA-GGGT3' (SJ-634) (SEQ.ID.NO.:18)

The italicized bases correspond to nucleotide positions 1 to 21 in the sequence reported in FIG. 4. The additional nucleotides 5' of this sequence in the primer are not identical to the promoter sequence, but were included in order to place a XbaI site at the 5' end of the amplification product. The XbaI (5'-TCTAGA-3') (SEQ.ID.NO.:19) site is underlined.

A second (3') primer was synthesized which had the following sequence:

3' primer 5'GGTTATCATTGTATGAACTGA3' (SJ-618) (SEQ.ID.NO.:20)

This primer contains the precise complement (shown in italics) to the sequence reported in FIG. 4 from bases 2343 to 2363. This primer was not designed with an additional restriction enzyme site due to the fact that a natural NcoI site (5'-CCATGG-3') (SEQ.ID.NO.:21) straddles the start codon betweenbase pairs 2034 and 2039, thereby allowing for insertion of the storage protein promoter into the appropriate cloning vector.

These two primers were used in a PCR amplification reaction to produce a DNA fragment containing the sequence between nucleotides 1 and 2342 of the flax seed storage protein gene with a XbaI site at the 5' end and a NcoI site 302 base pairs from the 3' end. PCR amplification was performed using the enzyme Pfu (Strategene) using conditions recommended by the enzyme manufacturer and a temperature program of 94° C. (denaturation) for 1 minute, 55° C. (annealing) for 1 minute, and 72° C. (elongation) for 3.5 minutes. The template was the legumin seed storage protein genomic clone shown in FIG. 4.

The resulting amplification product was subsequently digested with XbaI and NcoI to remove the desired 2 kb promoter region. This promoter fragment was cloned into the XbaI and NcoI sites of a XbaI and NcoI digested plasmid designated pGUS1318 (Plasmid pGUSN358S (Clontech Laboratories) was cut with NcoI and EcoRI and the GUS insert was cloned into pBluescriptKS+ (Stratagene) which was adapted to contain an NcoI site in the multiple cloning site.) The resulting plasmid containing the promoter-GUS fusion was called pPGUS1318. The terminator of the legumin seed storage protein from flax was also amplified from the above mentioned genomic clone. To perform the necessary PCR amplification, oligonucleotide primers were synthesized having the following sequences:

5' primer: 5'GC<u>AAGCTT</u>AATGTGACGGTGAAATAA-TAACGG3' (SJ620) (SEQ.ID.NO.:22)

The italicized bases correspond to nucleotide positions 3780 to 3803 in the sequence reported in FIG. 4. The additional nucleotides 5' of this sequence in the primer are not identical to the promoter sequence, but were included in order to place a HindIII site at the 5' end of the amplification product. The HindIII site (5'-AAGCTT-3') (SEQ.ID.NO.:23) is underlined.

A second (3') primer was synthesized which had the following sequence:

3' primer 5'TA<u>GGTACC</u>TGGCAGGTAAAGACTC-TGCTC3' (SJ-618) (SEQ.ID.NO.:24)

This primer contains the precise complement (shown in italics) to the sequence reported in FIG. 4 from bases 4311 to 4290. The additional nucleotides 5' of this sequence in the primer are not identical to the promoter sequence, but were included in order to place a KpnI site at the 5' end of the amplification product. The KpnI site (5'-GGTACC-3') (SEQ.ID.NO.:25) is underlined.

These two primers were used in a PCR amplification reaction to produce a DNA fragment containing the sequence between nucleotides 3779 and 4311 of the flax seed storage protein gene terminator with a HindIII site at the 5' end and a KpnI site at 3' end. Amplification using PCT was as described above. The above pPGUS1318 vector that contains the amplified promoter was digested with XhoI and treated with Klenow to create a blunt end. The vector was subsequently digested with KpnI and the above amplified terminator sequence was inserted so that it was located 3' of the GUS coding sequence. The resulting vector containing the flax seed storage protein promoter, GUS and the flax seed storage protein terminator is referred to as pPGUST.

The XbaI-KpnI insert of pPGUST which contains the linin promoter-GUS coding sequence-linin terminator sequence was ligated into the XbaI-KpnI sites of pSBS3000 (This vector is a derivative from the Agrobacterium binary plasmid pPZP221 (Hajdukiewicz et al., 1994, Plant Molec. Biol. 25: 989–994). In pSBS3000 the plant gentamycin resistance gene of pPZP221 was replaced with parsley ubiquitin promoter-phosphinothricin acetyl transferase gene-parsley ubiquitin termination sequence to confer resistance to the herbicide glufosinate ammonium). The resulting vector is called pSBS2089. In addition the XbaI-KpnI insert of pPGUST which contains the linin promoter-GUS coding sequence-linin terminator sequence was ligated into the XbaI-KpnI sites of the Agrobacterium binary plasmid pCGN1559 (MacBride and Summerfield, 1990, Plant Molec. Biol. 14 269–276, confers resistance to the antibiotic kanamycin)). The resulting vector was called pSBS2083. Plasmids pSBS2089 and pSBS2083 were electroporated into Agrobacterium strain EHA101. Agrobacterium strain EHA101 (pSBS2089) was used to transform flax and Arabidopsis, Agrobacterium strain EHA101 (pSBS2083) was used to transform Brassica napus. Flax transformation was performed essentially as described in Jordan and McHughen (1988) Plant cell reports 7: 281–284, except transgenic shoots were selected on 10 μM L-phosphinothricine instead of kanamycin. Arabidopsis transformation was done essentially as described in "Arabidopsis Protocols; Methods in Molecular Biology" Vol 82. Edited by Martinez-Zapater J M and Salinas J. ISBN 0-89603-391-0 pg 259–266 (1998) except the putative transgenic plants were selected on agarose plates containing 80 μM L-phosphinothricine. Brassica napus transformation was done essentially as described in Moloney et al. (1989). Plant Cell Reports 8: 238–242.

Figure 10:
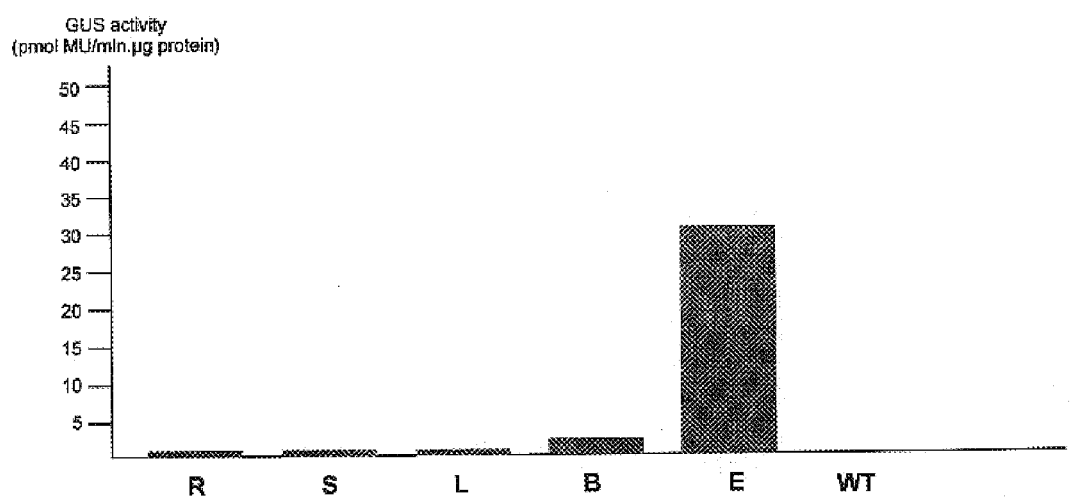
FIG. 10 shows the tissue-specific expression of GUS in transgenic flax plants transformed with a linin promoter-GUS-linin terminator gene construct.

FIG. 10 shows the tissue-specific expression of GUS in transgenic flax plants transformed with a linin-GUS gene construct (pSBS2089). GUS expression was measured in roots (R), stems (S), leaves (L), Buds (B) and embryo (E). Some expression was seen in buds, and maximal expression was achieved in embryo tissues. No detectable expression was seen in any of the untransformed (WT) tissues.

Figure 11:
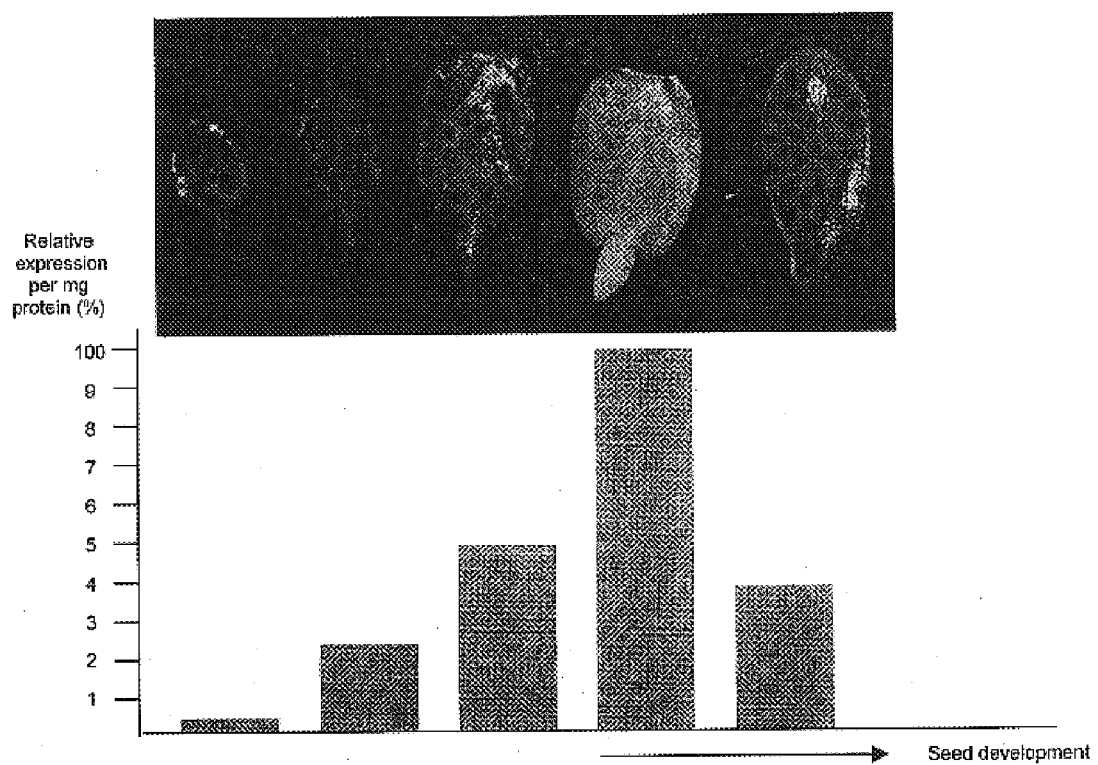
FIG. 11 shows the temporal expression of GUS in transgenic flax plants transformed a linin promoter-GUS-linin terminator gene construct.

FIG. 11 shows the temporal expression of GUS in transgenic flax plants transformed with a linin-GUS gene construct (pSBS2089). As can be seen, maximum expression is achieved in mature (pre-dessicated) flax embryos.

Figure 12:
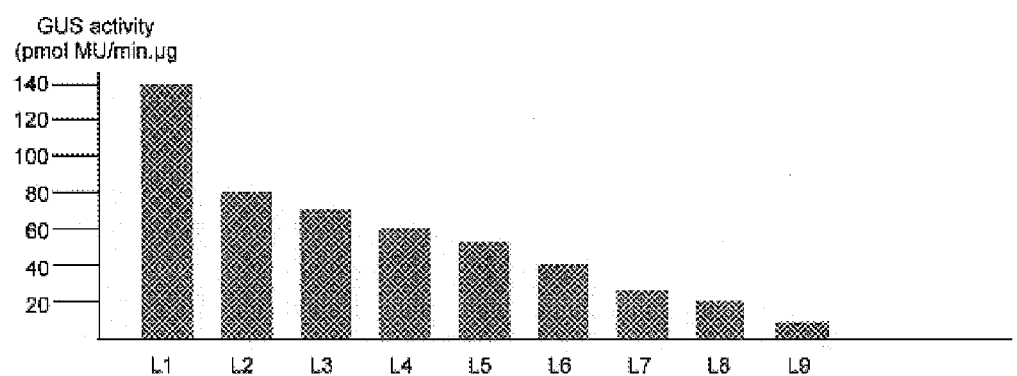
FIG. 12 shows the expression of GUS in transgenic *Brassica napus* plants (L1 to L9) transformed with a linin promoter-GUS-linin terminator gene construct.

FIG. 12 shows the absolute expression of GUS in transgenic Brassica napus plants (L1 to L9) transformed with a linin-GUS gene construct (pSBS2083). As can be seen high level expression can be achieved in Brassica napus plants. When comparing individual transgenic plants, a typical variation in expression due to position effect can also be seen.

Figure 13:
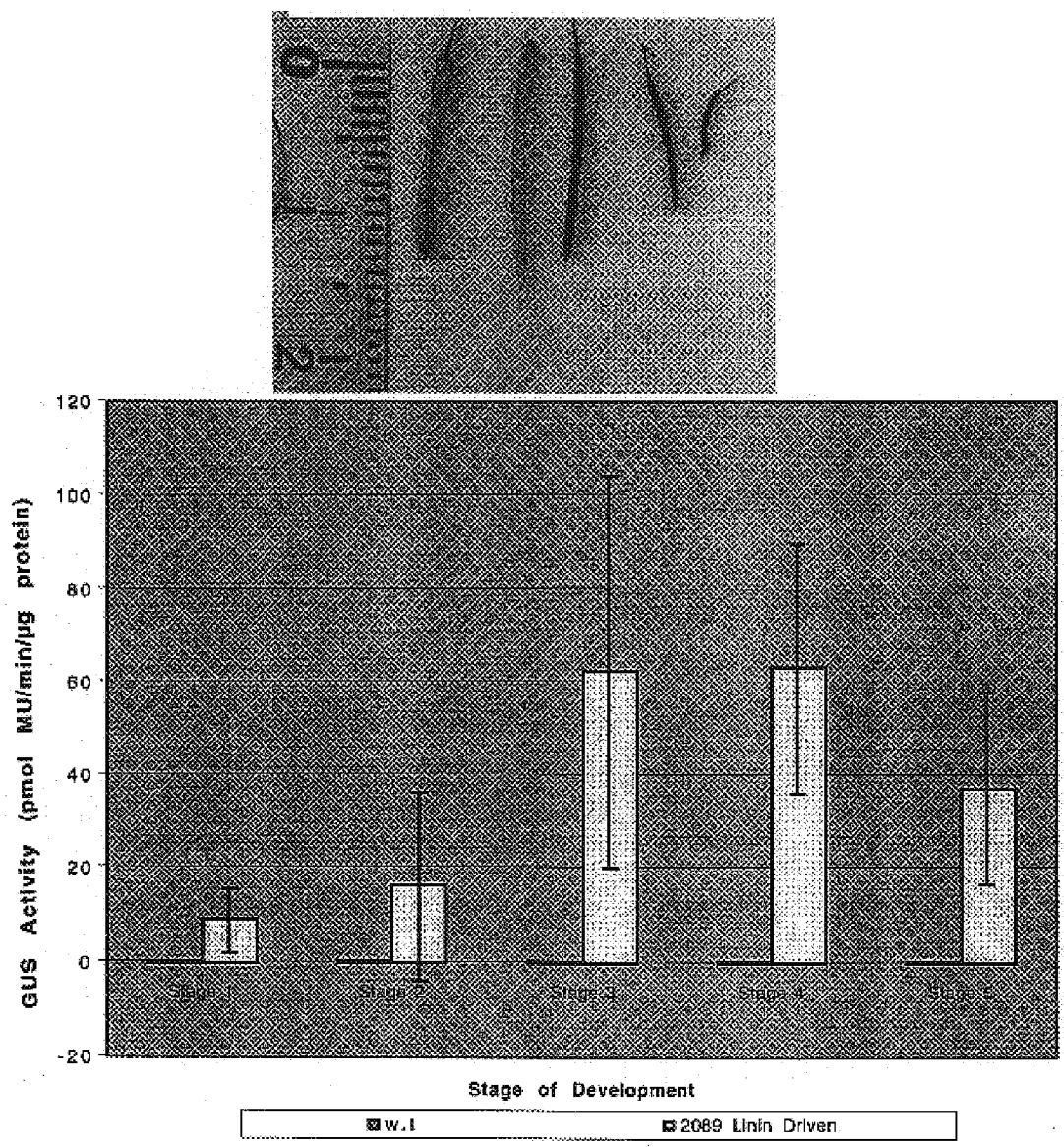
FIG. 13 shows the expression of GUS in transgenic Arabidopsis plants transformed with a linin promoter-GUS-linin terminator gene construct at different stages of seed development.

FIG. 13 shows expression of GUS in transgenic Arabidopsis siliques (transformed with a linin-GUS gene construct (pSBS2089)) during seed development. As can be seen high level expression can also be achieved in Arabidopsis seed tissues. Maximum expression is achieved at stage 4 (mature but not fully dessicated) of seed development. No detectable expression is observed in non-seed tissues such as leaves, stems, roots and silique walls (results not shown).

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

SEQUENCE LISTING

<160> NUMBER OF SEQ ID NOS: 25

<210> SEQ ID NO 1
<211> LENGTH: 4305
<212> TYPE: DNA
<213> ORGANISM: Linum usitatissimum

<400> SEQUENCE: 1

```
ttcaaaaccc gattcccgag gcggccctat tgaagatatg ggggaagttc gacgagatcg      60
atgtcgggtc gagtgctatg gtgatggtgc cgtttggggg gaggatgagc gagatagcca     120
agactagcat tccgttccca cacagagttg ggaatttgta ccaaatccaa cacttgtcgt     180
attggagcga cgatagggac gcggaaaaac acatccgttg gatcagggag ttgtacgatg     240
atctcgagcc ttatgtgtcg aagaatccga ggtatgctta cgtgaactac agggatctcg     300
acatcgggat gaatggagga ggtgaagggg atgagaaggg tacttatggt gaggctaagg     360
tgtgggggga gaagtacttt ggggtcaact tgatcggtt ggttcgggtg aagacgattg     420
ttgatcccaa taatgtgttt cgaaacgagc agagcattcc ctcaattcca actcggttat     480
aaggatcaat gatcaatgag aattttcctt tccaatgtga ttacaagttc tattgggtca     540
gctttctcaa ctgctcctat tcatttagat taattcataa caactattaa tttaccagcc     600
ttttatccgg cccgttggcc gatttatttt cttaagtttt agatgaaatg aaaccgattt     660
agtttttatt gagatgagat taatcttaat ttgcttgaaa tttactcacg gttgatgtga     720
tatttggaat taactaaaat gataaatatc ggataaaaat aaaatatttt aaaataaata     780
acataaacat aagaacaata aaataaataa atttaatttt aatttatttc cttgttttct     840
ttctgtatca tacatctctt ctcttacttc ttaaaggctt ttcaattatc acttaattaa     900
atacaataga taaatcgtta attctataac attaacctat acacttgcac ggtgaacaat     960
caatatgata atataataat aatataataa ttcaattatt aatctacaat tttttaatta    1020
taaagtttat gcggtcagtt tctgcaagct ccgagctcct tgtcatcgtt agtttctgcg    1080
gtctcaaggt ataacgactc ggagcgacga gcccttttgct tccaatggac gggttgcatt    1140
tctgccgtcg ttgagctcga ttggcgtgtc atgctggagt cagagttcct acaaaaaaac    1200
cctaaactag agggtgatta gggtgaaatt agggtgttgg cctgggttcc attgtccaaa    1260
gttttagtca acttaaaaac agacttaaat tttatgcttc aaaatagttt atctgttatt    1320
atattagcgt gtaattagtc ttgacaatgg ggccggacgg gtacggattc gggaccccga    1380
tccccgccca tagtgtaatg gctcaactgc caagtcagca ttggaccgaa attattggac    1440
acgaagtact aatgtgaaaa actttacatt tgttattttc tactttaata ctatgctatt    1500
ttcaaaattt gaactttaat actatgtttt tatatagttt agtatatctt aatttttatg    1560
caaattcatc taattgtatt aaactatttt cgatccgtag ctaattattt cgaaggcaag    1620
tcaaagtgtt attgtggact atgtgagcta atattgaacc tttatctctc ccaaccactc    1680
aagttaattg aaccaaactc gatcggttgg gtttcgagct atttcgagcc attgttgtta    1740
tatgcacgtg agatatcaag attgacccga acactttatt atgataatgt agaaaagaa     1800
aacatattct aagactacat gcatgcaaag tgcaaccct gcatggaaag ctgctcaaca    1860
cgtggcatag actcccgcca cgtgtccatt ccacctcatc acctcacccc caccgttcac    1920
ctcttattat atcacaacaa tcaatcaatc ctactcctcc atactcgaac aaatccgacc    1980
aacttatacc aatattccca aacttgatta atttctcagc aatatggatc agacgcacca    2040
```

-continued

```
gacatacgcc ggaaccacgc agaacccgag ctatggcggc gggggcacaa tgtaccagca      2100
gcagcagccg aggtcttacc aggcggtgaa ggcggccact gcagccaccg cgggtggatc      2160
cctcatcgtt ctgtccggtc tcatccttac ggccaccgtc atttcactca tcatagccac      2220
ccctctcctt gtcatcttca gccctgttct tgtcccggct ctcatcaccg tcgggctctt      2280
gatcaccggg tttcttgctt ccggtgggtt cggagtcgcc gccgtcaccg tcttgtcctg      2340
gatctatagg tatgtataag ctttggactt tagtattgtt ataaaataca taagctgatt      2400
tatgaacatg gatctcccaa caagagttat ttaaatgcat tctcggtctg actcgatcgg      2460
ttgggttttg agctactcgg tcacaatggt cgggtcggct ctggatctgt tatactaata      2520 tttgaagcc tgaagtttca ttgttctgcc ccaacttccc actacctttt gagggtgtta      2580
agaagccata caaactaatt atgaatccct cccaacaact cagaactcga gtcagtgggt      2640
tgtgacggtt ctctataaac atttcgaaaa tctttgttca atgaacgtag aaatgaccat      2700
gcttgatgat tgtgggtctt ataaggtacg tgaccggcgg gcacccggcg ggagggatt       2760 cgctggacca ggctaggtcg aagctggccg aaaggccag ggaggtgaag gacagggcgt       2820
cggagttcgc acagcagcat gtcacaggtg gtcaacagac ctcttaaaga gagtcctcta     2880
gttaaattgg tcttcgtttc tgtttcgtgg cggcttgtaa actctctttt aagtgtgctg      2940
ttttcctttt gtctcgtgtg ttgtaagtga aagtgtaatc gaagttccaa gttggagatg      3000
tttgtaacga tgatgttttc taataatcag agatattaaa agggttgcta atttagtatt      3060
gcgtctgatc tcgaccaaa ctcgcaagta aaattgcaga ggatgagttg tacagaacaa       3120
gcgtgcattg ttctggaagt tcatctcctt ggagccgacc ttgttgcttg cagtttcgcc     3180
aagtccacta gacaatgtta cgagttaagc ctctgtcaaa cagatcgctc tagcgtccca     3240
gaaaacacca gattttcga aaccatcgg ggatcaattt tcgattcaat tccgatcttg       3300
gaagtacttg aacagaagca tgatgctaaa agataataga aaatcgaagc ctagaaaagt    3360
tgtacagaaa gcaacaagtc aaaaatatag atcaacttca aaggttcaaa ttacatctta    3420
cagaccccaa aaatgacag ttaacagaag tcgactaaac agaaaccagc cagcttcacc     3480
tggaatgaag gagctttgat caatccatcc tagcttcatt cccctttgaa attgcagaca    3540
gagctctcat cctgctaaag ctggtggctt attcttaacc ctgcaatcaa taagcatgaa   3600
ctaacattgg acaccttcat cggcggattg ctcgaaaatc agtgagcgag ggatttacct   3660
gtgtgtgtag taacctctct ccttgtacat aaaatctgga aattccggca tcaactactg   3720
ccacctttct gcttaaggtg attttatcac caaggctgag cgtgattcct tgcgtcttgc   3780
tccgaatcct gatgtatcca ctgagctttc catctcctc cttctccagg cttatgttca    3840
ccaatgcgtc ctcgccgaac acactcttgg cgtacaagtt cgcagccagg aatccacact   3900
ctccatcaag tgcagacctg caaaccccaa ataagaacac aaactccaaa gtcaacgatc    3960
aattctccgc cttttatgaa gaaaaggaaa cttctgggta cttacggtgc cgtcagacac   4020
ttcatatttg tagacttgat gatatggtcc aggaattcct tctcgttctg aattgttgtg  4080
ttaacagcaa cctgacagac agaaagatat cgcaaattta agatactggg atgactaggc  4140
acagagaaat gaaatctaat tctagaagta aaaccttatt ttcccattca aattctgccc   4200
acatagtccg gaacgcagca tccgagcaag aagcaggaga gatgtaatcc atgatatcga   4260
tgtggatatc gttgaggacg acaactgaac gttccatcac attgg                   4305
```

<210> SEQ ID NO 2

```
<211> LENGTH: 109
<212> TYPE: PRT
<213> ORGANISM: Linum usitatissimum

<400> SEQUENCE: 2

Met Asp Gln Thr His Gln Thr Tyr Ala Gly Thr Thr Gln Asn Pro Ser
  1               5                  10                  15

Tyr Gly Gly Gly Thr Met Tyr Gln Gln Gln Pro Arg Ser Tyr
             20                  25                  30

Gln Ala Val Lys Ala Ala Thr Ala Ala Thr Ala Gly Gly Ser Leu Ile
         35                  40                  45

Val Leu Ser Gly Leu Ile Leu Thr Ala Thr Val Ile Ser Leu Ile Ile
     50                  55                  60

Ala Thr Pro Leu Leu Val Ile Phe Ser Pro Val Leu Val Pro Ala Leu
 65                  70                  75                  80

Ile Thr Val Gly Leu Leu Ile Thr Gly Phe Leu Ala Ser Gly Gly Phe
                 85                  90                  95

Gly Val Ala Ala Val Thr Val Leu Ser Trp Ile Tyr Arg
            100                 105

<210> SEQ ID NO 3
<211> LENGTH: 46
<212> TYPE: PRT
<213> ORGANISM: Linum usitatissimum

<400> SEQUENCE: 3

Tyr Val Thr Gly Gly His Pro Ala Gly Gly Asp Ser Leu Asp Gln Ala
  1               5                  10                  15

Arg Ser Lys Leu Ala Gly Lys Ala Arg Glu Val Lys Asp Arg Ala Ser
             20                  25                  30

Glu Phe Ala Gln Gln His Val Thr Gly Gly Gln Gln Thr Ser
         35                  40                  45

<210> SEQ ID NO 4
<211> LENGTH: 3501
<212> TYPE: DNA
<213> ORGANISM: Linum usitatissimum

<400> SEQUENCE: 4
tctagacatt tgacataaac cgaattcaaa gaacacaaca ttgactaaca ccaaaaagaa      60
atagagtagt gaaatttgga agattaaaaa atagaaacaa actgattctt agaaagaaga    120
gatgattagg tgctttcagt tcggtctgtc aggaaatcga gatgttcact tatttacatt    180
gtcgattcat ctcccaattg tcctggttcc tttactgtcc gacgctttttt tgaatcccag   240
ttaattccca tcaagtcttc cttcagctgc gtagcactgc tagctccaac atggagcgtg    300
gagtctactc gttcatgggg catcgcaaag gtttgccttc atgttctgct accagccagc    360
gcccaccgcc tcttggttgt gtggacaatt gcggtgaagc gcgcaagttg acatcccata    420
gtctcgacac ttcaccatat ggatgtttaa aacgtatatc acgagtgcga tctacatgtc    480
ccatcacacc acatataaag caatagtttg ggagctttttc atatttgaaa cgggcattga    540
cgacttgccc tctcgataat ttaatctttt tttctcttca gctgattgtg tgcatccatt    600
cgggctcaga agcacatcaa aggatctctc ccatcgtagt attgggtcgt gtcgtatgat    660
acgaagcagt cgatgaagtt tcctaatgtg cgagctacag gctccgcaaa gaacccgcga    720
ggtagatcgt atgctagtac ccaaaaatca gtttgtcgta gcggaatcaa cactagagac    780
tcaccctaat gcatctcatg tgtgatgaac agtttatcat ttgtgagtct agggtcattt    840
```

```
gtcgatgacc caatgcacat tgagcttatg atagaatttg aataggaagc gttttccacc     900
cagatcacga atagctaccc cttttcggg cgccaaattt ccggcatcct atcttccacc      960
acaacttaaa gatgcgatcg gtaaggaact caccgaccac acacatcgaa taatcttcgg    1020
tgaccggttc ctgttgatca agtccctcaa tttcctcaac ctagtcttca atcgccgcta    1080
gcgttatccc ccgcatatgg actttcatag cgcggagcgt agccggagac gacgagcaag    1140
aaggatgagc ggcggcagat tgcggctaaa gaaacgagct tcctgccttg ctctatggag    1200
gcagatttct gagttgatgg tgatggattt gtgatgtgga cacttttaat ttaagttgat    1260
ttttttagcac ttcattcacg taattaaata ataatttcc agtattttat atttatttcc    1320
ttacgttatc taatttttg aaagattaaa actttgatat aggcaagatc atgacacgtc     1380
gaagttaagt gaatgagact cctaacaagg taataacaaa gcagttcata aaccgaatga    1440
ccttgatctt tactaagctt gagatcattg aacatataat taaatacgtt aatgaaagat    1500
aagaacttta atataaaaat cattcaaaac gagaaactga taacaaaaac aaagcaaacg    1560
gccaacaaaa taatagacgg tggaaggatg atgcagagcc atccacccctt tttcccagt    1620
ttccttactg cttacttctc tatgcatatc acaagacgcc cttgaaactt gttagtcatg    1680
cagagccctt actcgccagg tcaccgcacc acgtgttact ctatcacttc tcctcccttt    1740
cctttaaaga accaccacgc cacctccctc tcacaaacac tcataaaaaa accacctctt    1800
gcatttctcc caagttcaaa ttagttcaca gctaagcaag aactcaacaa caatggcgga    1860
tcgtacaaca cagccacacc aagtccaggt ccacacccag caccactatc ccaccggcgg    1920
ggctttcggc cgttatgaag gtggactcaa aggcggtcca catccaccagc aaggatcagg    1980
cagcggccca tcagcttcca aggtgttagc agtcatgacc gcgctcccca tcggcgggac    2040
cctccttgcc ttggccggga taaccttggc tgggacgatg atcgggctgg cgatcaccac    2100
cccgattttt gtcatctgca gccctgttct agtcccggcc gctctgctca tcgggttgc    2160
cgtgagcgcg tttctggcct cggggatggc cgggctgaca gggctgacct cgctgtcgtg    2220
gtttgcgagg tatctgcagc aggctgggca gggagttgga gtgggggtgc cggatagttt    2280
cgagcaggcg aagaggcgca tgcaggatgc tgctgggtat atggggcaga agaccaagga    2340
agttgggcag gagatccaga ggaagtctca ggatgtgaaa gcatcagaca aataaggtga    2400
taataagggg ttttgggttc gtgtgtaaac tggtaaaatg gaaattctgg gttttactgt    2460
acttttgcat gtagtggaat gaatgagttc ttgttctctt ttgtcttta atcataaagt     2520
aagaagcagc atttcatgtt ctggttgaat attgtcaaga attcgcaaca aatttagcta    2580
aaccagttca atcttaccgg ttagacgact tcccagtaag aaacattcca ggtccatccc    2640
ggtataagag tctggacttc tgaaaccttt agaccttgga tttggaaaaa agatgaaacc    2700
tttagaataa attacaacga tggcagattg tacaaaactg gagtcgagat catgtaaatt    2760
agcccataac taagaaccgg cgatgacaac aattactagg aatatggttg ttgggctggt    2820
cggcggctag cggtgatgat ttggaagaat cggggatcca gaatgtgaga accgaatcat    2880
cgacgaacat tacccggcga ggagcccatt tcaagcaact ttggaactcc tatatggctg    2940
ttccagcagg ccacctgctc aagaaagaaa gaagccatgt cagaaatcct tacgaaatct    3000
aactggatgc tgatatgaat ccgccaggtg tgcggagttc tttacaggca ggatctataa    3060
agaagaaaca tgttttgtat tggcattgtt gatgttccaa gcacgcagcg atctatctcc    3120
ggatcctaac aacaaaaata cggattctgt aagaaacaag cgcagaaaac ttctgcaacg    3180
```

| | |
|---|---:|
| aaaccactcg tatatttggt tctgagttgg agaaagatga ccatactact gtatttggtt | 3240 |
| gaacttggat tggaaccgaa attttgagtt gaaaagcgag tgatcgtata taaatttcag | 3300 |
| attcagatta ggatatccta tgagagaagg tagagttacc tgatactaca tactgcccat | 3360 |
| cagggtaaa agttgcctcg atggttgtgt ttggagatgg ttccaggcta aatccacaac | 3420 |
| gctgaacaaa ttaaagatg aatggatcaa tcttcaaccc ttacttctgc atttatgagg | 3480 |
| attggctcaa ggctctctag a | 3501 |

<210> SEQ ID NO 5
<211> LENGTH: 180
<212> TYPE: PRT
<213> ORGANISM: Linum usitatissimum

<400> SEQUENCE: 5

```
Met Ala Asp Arg Thr Thr Gln Pro His Gln Val Gln Val His Thr Gln
  1               5                  10                  15
His His Tyr Pro Thr Gly Gly Ala Phe Gly Arg Tyr Glu Gly Gly Leu
             20                  25                  30
Lys Gly Gly Pro His His Gln Gln Gly Ser Gly Ser Gly Pro Ser Ala
         35                  40                  45
Ser Lys Val Leu Ala Val Met Thr Ala Leu Pro Ile Gly Gly Thr Leu
     50                  55                  60
Leu Ala Leu Ala Gly Ile Thr Leu Ala Gly Thr Met Ile Gly Leu Ala
 65                  70                  75                  80
Ile Thr Thr Pro Ile Phe Val Ile Cys Ser Pro Val Leu Val Pro Ala
                 85                  90                  95
Ala Leu Leu Ile Gly Phe Ala Val Ser Ala Phe Leu Ala Ser Gly Met
            100                 105                 110
Ala Gly Leu Thr Gly Leu Thr Ser Leu Ser Trp Phe Ala Arg Tyr Leu
        115                 120                 125
Gln Gln Ala Gly Gln Gly Val Gly Val Gly Val Pro Asp Ser Phe Glu
    130                 135                 140
Gln Ala Lys Arg Arg Met Gln Asp Ala Ala Gly Tyr Met Gly Gln Lys
145                 150                 155                 160
Thr Lys Glu Val Gly Gln Glu Ile Gln Arg Lys Ser Gln Asp Val Lys
                165                 170                 175
Ala Ser Asp Lys
            180
```

<210> SEQ ID NO 6
<211> LENGTH: 1676
<212> TYPE: DNA
<213> ORGANISM: Linum usitatissimum

<400> SEQUENCE: 6

| | |
|---|---:|
| tccactatgt aggtcatatc catcatttta attttgggc accattcaat tccatcttgc | 60 |
| ctttagggat gtgaatatga acggccaagg taagagaata aaataatcc aaattaaagc | 120 |
| aagagaggcc aagtaagata atccaaatgt acacttgtca tcgccgaaat tagtaaaata | 180 |
| cgcggcatat tgtattccca cacattatta aaataccgta tatgtattgg ctgcatttgc | 240 |
| atgaataata ctacgtgtaa gcccaaaaga acccacgtgt agcccatgca aagttaacac | 300 |
| tcacgacccc attcctcagt ctccactata taaacccacc atccccaatc ttaccaaacc | 360 |
| caccacacga ctcacaactc gactctcaca ccttaaagaa ccaatcacca ccaaaaaatg | 420 |
| gcaaagctga tgagcctagc agccgtagca acgcagttcc tcttcctgat cgtggtggac | 480 |

-continued

```
gcatccgtcc gaaccacagt gattatcgac gaggagacca accaaggccg cggtggaggc    540
aaggtggcag ggacagcagc agtctgcgag cagcagatcc agcagcgaga cttcctgagg    600
agctgccagc agttcatgtg ggagaaagtc cagaggggcg ccacagcca ctattacaac    660
cagggccgtg gaggaggcga acagagccag tacttcgaac agctgtttgt gacgacctta    720
agcaattgcg caccgcggtg caccatgcca ggggacttga agcgtgccat cggccaaatg    780
aggcaggaaa tccagcagca gggacagcag cagggacagc agcaggaagt tcagaggtgg    840
atccagcaag ctaaacaaat cgctaaggac ctccccggac agtgccgcac ccagcctagc    900
caatgccagt tccagggcca gcagcaatct gcatggtttt gaagggtgga tcgattatga    960
gatcgtacaa agacactgct aggtgttaag gatggataat aataataata atgagatgaa   1020
tgtgttttaa gttagtgtaa cagctgtaat aaagagagag agagagagag agagagagag   1080
agagagagag agagagagag agaggctgat gaaatgttat gtatgtttct tggttttttaa   1140
aataaatgaa agcacatgct cgtgtggttc tatcgaatta ttcggcggtt cctgtgggaa   1200
aaagtccaga agggcggccg cagctactac tacaaccaag gccgtggagg agggcaacag   1260
agccagcact tcgatagctg ctgcgatgat cttaagcaat tgaggagcga gtgcacatgc   1320
aggggactgg agcgtgcaat cggccagatg aggcaggaca tccagcagca gggacagcag   1380
caggaagttg agaggtggtc ccatcaatct aaacaagtcg ctagggacct tccgggacag   1440
tgcggcaccc agcctagccg atgccagctc caggggcagc agcagtctgc atggttttga   1500
agtggtgatc gatgagatcg tataaagaca ctgctaggtg ttaaggatgg gataataaga   1560
tgtgttttaa gtcattaacc gtaataaaaa gagagagagg ctgatggaat gttatgtatg   1620
tatgtttctt ggttttttaaa attaaatgga aagcacatgc tcgtgtgggt tctatc      1676
```

<210> SEQ ID NO 7
<211> LENGTH: 174
<212> TYPE: PRT
<213> ORGANISM: Linum usitatissimum

<400> SEQUENCE: 7

```
Met Ala Lys Leu Met Ser Leu Ala Ala Val Ala Thr Gln Phe Leu Phe
 1               5                  10                  15

Leu Ile Val Val Asp Ala Ser Val Arg Thr Thr Val Ile Ile Asp Glu
            20                  25                  30

Glu Thr Asn Gln Gly Arg Gly Gly Lys Val Ala Gly Thr Ala Ala
        35                  40                  45

Val Cys Glu Gln Gln Ile Gln Gln Arg Asp Phe Leu Arg Ser Cys Gln
    50                  55                  60

Gln Phe Met Trp Glu Lys Val Gln Arg Gly Gly His Ser His Tyr Tyr
65                  70                  75                  80

Asn Gln Gly Arg Gly Gly Glu Gln Ser Gln Tyr Phe Glu Gln Leu
                85                  90                  95

Phe Val Thr Thr Leu Ser Asn Cys Ala Pro Arg Cys Thr Met Pro Gly
            100                 105                 110

Asp Leu Lys Arg Ala Ile Gly Gln Met Arg Gln Glu Ile Gln Gln Gln
        115                 120                 125

Gly Gln Gln Gln Gly Gln Gln Glu Val Gln Arg Trp Ile Gln Gln
    130                 135                 140

Ala Lys Gln Ile Ala Lys Asp Leu Pro Gly Gln Cys Arg Thr Gln Pro
145                 150                 155                 160
```

```
Ser Gln Cys Gln Phe Gln Gly Gln Gln Gln Ser Ala Trp Phe
            165                 170
```

```
<210> SEQ ID NO 8
<211> LENGTH: 4999
<212> TYPE: DNA
<213> ORGANISM: Linum usitatissimum
<220> FEATURE:
<221> NAME/KEY: misc_feature
<222> LOCATION: (4396)
<223> OTHER INFORMATION: n is any nucleotide (atgc)
<221> NAME/KEY: misc_feature
<222> LOCATION: (4407)
<223> OTHER INFORMATION: n is any nucleotide (atgc)
<221> NAME/KEY: misc_feature
<222> LOCATION: (4415)
<223> OTHER INFORMATION: n is any nucleotide (atgc)
<221> NAME/KEY: misc_feature
<222> LOCATION: (4423)
<223> OTHER INFORMATION: n is any nucleotide (atgc)
<221> NAME/KEY: misc_feature
<222> LOCATION: (4445)
<223> OTHER INFORMATION: n is any nucleotide (atgc)
<221> NAME/KEY: misc_feature
<222> LOCATION: (4475)
<223> OTHER INFORMATION: n is any nucleotide (atgc)
<221> NAME/KEY: misc_feature
<222> LOCATION: (4497)
<223> OTHER INFORMATION: n is any nucleotide (atgc)
<221> NAME/KEY: misc_feature
<222> LOCATION: (4515)
<223> OTHER INFORMATION: n is any nucleotide (atgc)
<221> NAME/KEY: misc_feature
<222> LOCATION: (4545)
<223> OTHER INFORMATION: n is any nucleotide (atgc)
<221> NAME/KEY: misc_feature
<222> LOCATION: (4548)
<223> OTHER INFORMATION: n is any nucleotide (atgc)
<221> NAME/KEY: misc_feature
<222> LOCATION: (4550)
<223> OTHER INFORMATION: n is any nucleotide (atgc)
<221> NAME/KEY: misc_feature
<222> LOCATION: (4552)
<223> OTHER INFORMATION: n is any nucleotide (atgc)
<221> NAME/KEY: misc_feature
<222> LOCATION: (4556)
<223> OTHER INFORMATION: n is any nucleotide (atgc)
<221> NAME/KEY: misc_feature
<222> LOCATION: (4567)
<223> OTHER INFORMATION: n is any nucleotide (atgc)
<221> NAME/KEY: misc_feature
<222> LOCATION: (4580)
<223> OTHER INFORMATION: n is any nucleotide (atgc)
<221> NAME/KEY: misc_feature
<222> LOCATION: (4587)
<223> OTHER INFORMATION: n is any nucleotide (atgc)
<221> NAME/KEY: misc_feature
<222> LOCATION: (4591)
<223> OTHER INFORMATION: n is any nucleotide (atgc)
<221> NAME/KEY: misc_feature
<222> LOCATION: (4593)
<223> OTHER INFORMATION: n is any nucleotide (atgc)
<221> NAME/KEY: misc_feature
<222> LOCATION: (4605)
<223> OTHER INFORMATION: n is any nucleotide (atgc)
<221> NAME/KEY: misc_feature
<222> LOCATION: (4613)
<223> OTHER INFORMATION: n is any nucleotide (atgc)
<221> NAME/KEY: misc_feature
<222> LOCATION: (4616)
<223> OTHER INFORMATION: n is any nucleotide (atgc)
<221> NAME/KEY: misc_feature
<222> LOCATION: (4620)
<223> OTHER INFORMATION: n is any nucleotide (atgc)
<221> NAME/KEY: misc_feature
<222> LOCATION: (4622)
<223> OTHER INFORMATION: n is any nucleotide (atgc)
<221> NAME/KEY: misc_feature
```

-continued

```
<222> LOCATION: (4626)
<223> OTHER INFORMATION: n is any nucleotide (atgc)
<221> NAME/KEY: misc_feature
<222> LOCATION: (4635)
<223> OTHER INFORMATION: n is any nucleotide (atgc)
<221> NAME/KEY: misc_feature
<222> LOCATION: (4657)
<223> OTHER INFORMATION: n is any nucleotide (atgc)
<221> NAME/KEY: misc_feature
<222> LOCATION: (4659)
<223> OTHER INFORMATION: n is any nucleotide (atgc)
<221> NAME/KEY: misc_feature
<222> LOCATION: (4664)
<223> OTHER INFORMATION: n is any nucleotide (atgc)
<221> NAME/KEY: misc_feature
<222> LOCATION: (4668)
<223> OTHER INFORMATION: n is any nucleotide (atgc)
<221> NAME/KEY: misc_feature
<222> LOCATION: (4677)
<223> OTHER INFORMATION: n is any nucleotide (atgc)
<221> NAME/KEY: misc_feature
<222> LOCATION: (4685)
<223> OTHER INFORMATION: n is any nucleotide (atgc)
<221> NAME/KEY: misc_feature
<222> LOCATION: (4695)
<223> OTHER INFORMATION: n is any nucleotide (atgc)
<221> NAME/KEY: misc_feature
<222> LOCATION: (4705)
<223> OTHER INFORMATION: n is any nucleotide (atgc)
<221> NAME/KEY: misc_feature
<222> LOCATION: (4708)
<223> OTHER INFORMATION: n is any nucleotide (atgc)
<221> NAME/KEY: misc_feature
<222> LOCATION: (4711)
<223> OTHER INFORMATION: n is any nucleotide (atgc)
<221> NAME/KEY: misc_feature
<222> LOCATION: (4713)
<223> OTHER INFORMATION: n is any nucleotide (atgc)
<221> NAME/KEY: misc_feature
<222> LOCATION: (4715)
<223> OTHER INFORMATION: n is any nucleotide (atgc)
<221> NAME/KEY: misc_feature
<222> LOCATION: (4731)
<223> OTHER INFORMATION: n is any nucleotide (atgc)
<221> NAME/KEY: misc_feature
<222> LOCATION: (4738)
<223> OTHER INFORMATION: n is any nucleotide (atgc)
<221> NAME/KEY: misc_feature
<222> LOCATION: (4740)
<223> OTHER INFORMATION: n is any nucleotide (atgc)
<221> NAME/KEY: misc_feature
<222> LOCATION: (4743)
<223> OTHER INFORMATION: n is any nucleotide (atgc)
<221> NAME/KEY: misc_feature
<222> LOCATION: (4746)
<223> OTHER INFORMATION: n is any nucleotide (atgc)
<221> NAME/KEY: misc_feature
<222> LOCATION: (4759)
<223> OTHER INFORMATION: n is any nucleotide (atgc)
<221> NAME/KEY: misc_feature
<222> LOCATION: (4766)
<223> OTHER INFORMATION: n is any nucleotide (atgc)
<221> NAME/KEY: misc_feature
<222> LOCATION: (4773)
<223> OTHER INFORMATION: n is any nucleotide (atgc)
<221> NAME/KEY: misc_feature
<222> LOCATION: (4780)
<223> OTHER INFORMATION: n is any nucleotide (atgc)
<221> NAME/KEY: misc_feature
<222> LOCATION: (4782)
<223> OTHER INFORMATION: n is any nucleotide (atgc)
<221> NAME/KEY: misc_feature
<222> LOCATION: (4784)
<223> OTHER INFORMATION: n is any nucleotide (atgc)
<221> NAME/KEY: misc_feature
<222> LOCATION: (4790)
<223> OTHER INFORMATION: n is any nucleotide (atgc)
<221> NAME/KEY: misc_feature
<222> LOCATION: (4792)
```

-continued

```
<223> OTHER INFORMATION: n is any nucleotide (atgc)
<221> NAME/KEY: misc_feature
<222> LOCATION: (4795)
<223> OTHER INFORMATION: n is any nucleotide (atgc)
<221> NAME/KEY: misc_feature
<222> LOCATION: (4802)
<223> OTHER INFORMATION: n is any nucleotide (atgc)
<221> NAME/KEY: misc_feature
<222> LOCATION: (4810)
<223> OTHER INFORMATION: n is any nucleotide (atgc)
<221> NAME/KEY: misc_feature
<222> LOCATION: (4813)
<223> OTHER INFORMATION: n is any nucleotide (atgc)
<221> NAME/KEY: misc_feature
<222> LOCATION: (4820)
<223> OTHER INFORMATION: n is any nucleotide (atgc)
<221> NAME/KEY: misc_feature
<222> LOCATION: (4822)
<223> OTHER INFORMATION: n is any nucleotide (atgc)
<221> NAME/KEY: misc_feature
<222> LOCATION: (4830)
<223> OTHER INFORMATION: n is any nucleotide (atgc)
<221> NAME/KEY: misc_feature
<222> LOCATION: (4839)
<223> OTHER INFORMATION: n is any nucleotide (atgc)
<221> NAME/KEY: misc_feature
<222> LOCATION: (4843)
<223> OTHER INFORMATION: n is any nucleotide (atgc)
<221> NAME/KEY: misc_feature
<222> LOCATION: (4845)
<223> OTHER INFORMATION: n is any nucleotide (atgc)
<221> NAME/KEY: misc_feature
<222> LOCATION: (4847)
<223> OTHER INFORMATION: n is any nucleotide (atgc)
<221> NAME/KEY: misc_feature
<222> LOCATION: (4851)
<223> OTHER INFORMATION: n is any nucleotide (atgc)
<221> NAME/KEY: misc_feature
<222> LOCATION: (4854)
<223> OTHER INFORMATION: n is any nucleotide (atgc)
<221> NAME/KEY: misc_feature
<222> LOCATION: (4858)
<223> OTHER INFORMATION: n is any nucleotide (atgc)
<221> NAME/KEY: misc_feature
<222> LOCATION: (4865)
<223> OTHER INFORMATION: n is any nucleotide (atgc)
<221> NAME/KEY: misc_feature
<222> LOCATION: (4880)
<223> OTHER INFORMATION: n is any nucleotide (atgc)
<221> NAME/KEY: misc_feature
<222> LOCATION: (4882)
<223> OTHER INFORMATION: n is any nucleotide (atgc)
<221> NAME/KEY: misc_feature
<222> LOCATION: (4885)
<223> OTHER INFORMATION: n is any nucleotide (atgc)
<221> NAME/KEY: misc_feature
<222> LOCATION: (4887)
<223> OTHER INFORMATION: n is any nucleotide (atgc)
<221> NAME/KEY: misc_feature
<222> LOCATION: (4891)
<223> OTHER INFORMATION: n is any nucleotide (atgc)
<221> NAME/KEY: misc_feature
<222> LOCATION: (4893)
<223> OTHER INFORMATION: n is any nucleotide (atgc)
<221> NAME/KEY: misc_feature
<222> LOCATION: (4895)
<223> OTHER INFORMATION: n is any nucleotide (atgc)
<221> NAME/KEY: misc_feature
<222> LOCATION: (4901)
<223> OTHER INFORMATION: n is any nucleotide (atgc)
<221> NAME/KEY: misc_feature
<222> LOCATION: (4906)
<223> OTHER INFORMATION: n is any nucleotide (atgc)
<221> NAME/KEY: misc_feature
<222> LOCATION: (4927)
<223> OTHER INFORMATION: n is any nucleotide (atgc)
<221> NAME/KEY: misc_feature
<222> LOCATION: (4931)
<223> OTHER INFORMATION: n is any nucleotide (atgc)
```

-continued

```
<221> NAME/KEY: misc_feature
<222> LOCATION: (4933)
<223> OTHER INFORMATION: n is any nucleotide (atgc)
<221> NAME/KEY: misc_feature
<222> LOCATION: (4937)
<223> OTHER INFORMATION: n is any nucleotide (atgc)
<221> NAME/KEY: misc_feature
<222> LOCATION: (4942)
<223> OTHER INFORMATION: n is any nucleotide (atgc)
<221> NAME/KEY: misc_feature
<222> LOCATION: (4945)
<223> OTHER INFORMATION: n is any nucleotide (atgc)
<221> NAME/KEY: misc_feature
<222> LOCATION: (4949)
<223> OTHER INFORMATION: n is any nucleotide (atgc)
<221> NAME/KEY: misc_feature
<222> LOCATION: (4951)
<223> OTHER INFORMATION: n is any nucleotide (atgc)
<221> NAME/KEY: misc_feature
<222> LOCATION: (4954)
<223> OTHER INFORMATION: n is any nucleotide (atgc)
<221> NAME/KEY: misc_feature
<222> LOCATION: (4958)
<223> OTHER INFORMATION: n is any nucleotide (atgc)
<221> NAME/KEY: misc_feature
<222> LOCATION: (4965)
<223> OTHER INFORMATION: n is any nucleotide (atgc)
<221> NAME/KEY: misc_feature
<222> LOCATION: (4968)
<223> OTHER INFORMATION: n is any nucleotide (atgc)
<221> NAME/KEY: misc_feature
<222> LOCATION: (4970)
<223> OTHER INFORMATION: n is any nucleotide (atgc)
<221> NAME/KEY: misc_feature
<222> LOCATION: (4975)
<223> OTHER INFORMATION: n is any nucleotide (atgc)
<221> NAME/KEY: misc_feature
<222> LOCATION: (4982)
<223> OTHER INFORMATION: n is any nucleotide (atgc)
<221> NAME/KEY: misc_feature
<222> LOCATION: (4989)
<223> OTHER INFORMATION: n is any nucleotide (atgc)
<221> NAME/KEY: misc_feature
<222> LOCATION: (4994)
<223> OTHER INFORMATION: n is any nucleotide (atgc)

<400> SEQUENCE: 8
```

| | | | | | |
|---|---|---|---|---|---|
| ctcaagcata | cggacaaggg | taaataacat | agtcaccaga | acataataaa | caaaaagtgc | 60 |
| agaagcaaga | taaaaaaatt | agctatggac | attcaggttc | atattggaaa | catcattatc | 120 |
| ctagtcttgt | gaccatcctt | cctcctgctc | tagttgagag | gccttgggac | taacgagagg | 180 |
| tcagttggga | tagcagatcc | ttatcctgga | ctagcctttc | tggtgtttca | gagtcttcgt | 240 |
| gccgccgtct | acatctatct | ccattaggtc | tgaagatgac | tcttcacacc | aacgacgttt | 300 |
| aaggtctcta | tcctactcct | agcttgcaat | acctggcttg | caatacctgg | agcatcgtgc | 360 |
| acgatgattg | gatactgtgg | aggaggagtg | tttgctgatt | tagagctccc | ggttgggtga | 420 |
| tttgacttcg | atttcagttt | aggcttgttg | aaattttca | ggttccattg | tgaagccttt | 480 |
| agagcttgag | cttccttcca | tgttaatgcc | ttgatcgaat | tctcctagag | aaaagggaag | 540 |
| tcgatctctg | agtattgaaa | tcgaagtgca | catttttttt | caacgtgtcc | aatcaatcca | 600 |
| caaacaaagc | agaagacagg | taatctttca | tacttatact | gacaagtaat | agtcttaccg | 660 |
| tcatgcataa | taacgtctcg | ttccttcaag | aggggtttc | cgacatccat | aacgacccga | 720 |
| agcctcatga | aagcattagg | gaagaacttt | tggttcttct | tgtcatggcc | tttataggtg | 780 |
| tcagccgagc | tcgccaattc | ccgtccgact | ggctccgcaa | atattcgaa | cggcaagtta | 840 |
| tggacttgca | accataactc | cacggtattg | agcaggacct | attgtgaaga | ctcatctcat | 900 |
| ggagcttcag | aatgtggttg | tcagcaaacc | aatgaccgaa | atccatcaca | tgacggacgt | 960 |

```
ccagtgggtg agcgaaacga aacaggaagc gcctatcttt cagagtcgtg agctccacac   1020
cggattccgg caactacgtg ttgggcaggc ttcgccgtat tagagatatg ttgaggcaag   1080
acccatctgt gccactcgta caattacgag agttgttttt tttgtgattt tcctaagttt   1140
ctcgttgatg gtgagctcat attctacatc gtatggtctc tcaacgtcgt ttcctgtcat   1200
ctgtatatcc cgtcatttgca tccacgtgcg ccgcctcccg tgccaagtcc ctaggtgtca   1260
tgcacgccaa attggtggtg gtgcgggctg ccctgtgctt cttaccgatg ggtggaggtt   1320
gagtttgggg gtctccgcgg cgatggtagt gggttgacgg tttggtgtgg gttgacggca   1380
ttgatcaatt tacttcttgc ttcaaattct ttggcagaaa acaattcatt agattagaac   1440
tggaaaccag agtgatgaga cggattaagt cagattccaa cagagttaca tctcttaaga   1500
aataatgtaa cccctttaga ctttatatat ttgcaattaa aaaataatt taacttttag    1560
actttatata tagtttttaat aactaagttt aaccactcta ttatttatat cgaaactatt   1620
tgtatgtctc ccctctaaat aaacttggta ttgtgtttac agaacctata atcaaataat   1680
caatactcaa ctgaagtttg tgcagttaat tgaagggatt aacggccaaa atgcactagt   1740
attatcaacc gaatagattc acactagatg gccatttcca tcaatatcat cgccgttctt   1800
cttctgtcca catatccct ctgaaacttg agagacacct gcacttcatt gtccttatta     1860
cgtgttacaa aatgaaaccc atgcatccat gcaaactgaa gaatggcgca agaaccttc    1920
ccctccattt cttatgtggc gaccatccat ttcaccatct cccgctataa aacaccccca   1980
tcacttcacc tagaacatca tcactacttg cttatccatc caaaagatac ccaccatggc   2040
tagatcatca agcccttttgc ttctctcact ctgcattttc gccattctct tccactcttc   2100
tctgggtagg cagcaattcc agcaggggaa cgagtgccag atcgacagga tcgacgcatc   2160
cgagccggac aaaaccatcc aggcagaagc tggcaccatc gaggtatggg accagaaccg   2220
ccagcaattc cagtgcgctg gtgttgccgt tgtaaggcgc accattgagc ccaaaggtct   2280
tctcttgcct ttctacagca acacccctca gctcatctac atcgttcaag gtataaatta   2340
aatcagttca tacaatgata accaccactt cgaatgtatt tatcaaatat caatgatcga   2400
tgcacctgta tgtgttgtgt atattcaggt aggggagtta caggaatcat gttcccakga   2460
tgtccagaga cattcgagga atcccagcag caaggacaac agggccaaca gggtagttcc   2520
caagaccagc accagaagat ccgccgcttc cgtgaaggtg acgtcattgc cgtccctgcc   2580
ggtgtagccc actggtccta caacgatggc aacgaaccag tcatggccat tgttgtccat   2640
gacacttcca gccacctcaa ccaactggac aacaaccca gggtatataa gcattgccgt    2700
agttgctaat aaattgcaca caattggaac tctattttca gtatctaata acttttttcct  2760
tttttggcag aacttctact tggcaggaaa cccgagagac gagttcgaac aatcgcagca   2820
aggaggcagg ctgagccgtg gggagagtga aggtggacga ggacgcaggg aacctcttca   2880
acctgcaaca acctcttctt gcggaatcga ctccaagctc atcgcggagg cgttcaatgt   2940
cgacgagaac gtggcaagga ggctacgag cgagaacgac aacagaggcc agatcgtccg     3000
agtcgaaggc gagctcgaca tcgtcagacc tccgaccagt atccaggagg agtcacagga   3060
gcagggaggt cgtggtggtg gccgctacta ctccaatgga gtggaggaga ccttctgctc   3120
catgagacta attgagaaca tcggcgatcc ttctcgggca gacattttca ctccagaagc   3180
cggccgcgtt agatccctca acagccacaa cctccccgtc ctgcaatgga tccagcttag   3240
cgccgagaga ggcgttctct acaatgtata gatctcactc acgcaccaac tctaaattga   3300
```

-continued

| | |
|---|---|
| atccctaatt atttaattca ccgatatctg accgaccggt ttgaattttg taggaagcga | 3360 |
| tcaggctgcc gcactggaac atcaacgcac acagcatagt gtacgcgatc agaggacaag | 3420 |
| ccagagtcca gatcgtgaac gaggaaggga attcggtgtt cgatggagtg ctgcaggaag | 3480 |
| gacaggtggt gacggtgccg cagaacttcg cggtggtaaa gagatcccag agcgagaggt | 3540 |
| ttgagtgggt ggcgttcaag accaacgaca acgcgatggt gaactcgcta gccgggagga | 3600 |
| catcggcagt aagggcgatc cccgcggatg tactggctaa cgcctggagg gtgtcgccgg | 3660 |
| aggaggcgag gagggtgaag ttcaacaggc aggagactca cttggctagc accaggggcc | 3720 |
| agtccaggtc gcccgggagg ttgaatgtcg tcaaggaggt gatcaacttg cttatgtaaa | 3780 |
| atgtgacggt gaataataa cggtaaaata tatgtaataa taataataat aaagccacaa | 3840 |
| agtgagaatg aggggaaggg gaatgtgta atgagccagt agccggtggt gctaattttg | 3900 |
| tatcgtattg tcaataaatc atgaattttg tggttttttat gtgttttttt aaatcatgaa | 3960 |
| tttaaattt tataaaataa tctccaatcg gaagaacaac attccatatc catggatgtt | 4020 |
| tctttaccca aatctagttc ttgagaggat gaagcatcac cgaacagttc tgcaactatc | 4080 |
| cctcaaaagc tttaaaatga acaacaagga acagagcaac gttccaaaga tcccaaacga | 4140 |
| aacatattat ctatactaat actatattat taattactac tgcccggaat cacaatccct | 4200 |
| gaatgattcc tattaactac aagccttgtt ggcggcggag aagtgatcgg cgcggcgaga | 4260 |
| agcagcggac tcggagacga ggccttggat gagcagagtc tttacctgcc agggcgtgaa | 4320 |
| ggggaagagc ggccttctgg agtaggagtt cagcaagcgg cggttccttg gcggagtaag | 4380 |
| cggacgtaag ggtggntgtc gacgtcntcg tttcnggagg cgnattcatg aagggttaaa | 4440 |
| gtcanatctg tagctctcga gtgctcaggg agccnaaaga cgttgggaaa ccgtcgncgt | 4500 |
| ttggggcatc agtcngcggg gcacgcttcc ctcctgctgc tccanaancn angtanattt | 4560 |
| aaaaganatg ggaaattaan taatggnaat nannaggagg attgnaacgg tcnganccgn | 4620 |
| angaanagtt tttanngggtt taaatactgg gggagtngna gccngccnct ggttccngtg | 4680 |
| tagangaaac caagnnccgg gaggnttnca nnngnnaggg agaaaaagga nncatttnan | 4740 |
| nangcngagg gacatgaanc ggtacngagc tgnggttcan nnancggcgn nnggnagtcc | 4800 |
| cnngggaccn ggntggggtn anaagggaan ggaacattng gtngnangga naanaccntt | 4860 |
| ttacnattgc ctttgcaggn nngtntnggc ncntncgggt nacatccgc tgcatgggct | 4920 |
| ttggggngcc nanaggnagc cncangggna nncngccncc ttgtncangn cgctnaagtt | 4980 |
| cnattgtana tggncgttg | 4999 |

<210> SEQ ID NO 9
<211> LENGTH: 96
<212> TYPE: PRT
<213> ORGANISM: Linum usitatissimum

<400> SEQUENCE: 9

Met Ala Arg Ser Ser Pro Leu Leu Leu Ser Leu Cys Ile Phe Ala
1               5                   10                  15

Ile Leu Phe His Ser Ser Leu Gly Arg Gln Gln Phe Gln Gln Gly Asn
            20                  25                  30

Glu Cys Gln Ile Asp Arg Ile Asp Ala Ser Glu Pro Asp Lys Thr Ile
        35                  40                  45

Gln Ala Glu Ala Gly Glu Val Trp Asp Gln Asn Arg Gln Gln Phe Gln
    50                  55                  60

Cys Ala Gly Val Ala Val Val Arg Arg Thr Ile Glu Pro Lys Gly Leu

```
                65                  70                  75                  80
Leu Leu Pro Phe Tyr Ser Asn Thr Pro Gln Leu Ile Tyr Ile Val Gln
                    85                  90                  95

<210> SEQ ID NO 10
<211> LENGTH: 85
<212> TYPE: PRT
<213> ORGANISM: Linum usitatissimum
<220> FEATURE:
<221> NAME/KEY: SITE
<222> LOCATION: (59)
<223> OTHER INFORMATION: n is any amino acid
<221> NAME/KEY: SITE
<222> LOCATION: (62)
<223> OTHER INFORMATION: n is any amino acid
<221> NAME/KEY: SITE
<222> LOCATION: (78)
<223> OTHER INFORMATION: n is any amino acid
<221> NAME/KEY: SITE
<222> LOCATION: (82)
<223> OTHER INFORMATION: n is any amino acid

<400> SEQUENCE: 10

Gly Arg Gly Val Thr Gly Ile Met Phe Pro Xaa Cys Pro Glu Thr Phe
  1               5                  10                  15

Glu Glu Ser Gln Gln Gln Gly Gln Gln Gly Gln Gln Gly Ser Ser Gln
                 20                  25                  30

Asp Gln His Gln Lys Ile Arg Arg Phe Arg Glu Gly Asp Val Ile Ala
             35                  40                  45

Val Pro Ala Gly Val Ala His Trp Ser Tyr Asn Asp Gly Asn Glu Pro
         50                  55                  60

Val Met Ala Ile Val Val His Asp Thr Ser Ser His Leu Asn Gln Leu
 65                  70                  75                  80

Asp Asn Asn Pro Arg
                 85

<210> SEQ ID NO 11
<211> LENGTH: 165
<212> TYPE: PRT
<213> ORGANISM: Linum usitatissimum

<400> SEQUENCE: 11

Asn Phe Tyr Leu Ala Gly Asn Pro Arg Asp Glu Phe Glu Gln Ser Gln
  1               5                  10                  15

Gln Gly Gly Arg Leu Ser Arg Gly Glu Ser Glu Gly Gly Arg Gly Arg
                 20                  25                  30

Arg Glu Pro Leu Gln Pro Ala Thr Thr Ser Ser Cys Gly Ile Asp Ser
             35                  40                  45

Lys Leu Ile Ala Glu Ala Phe Asn Val Asp Glu Asn Val Ala Arg Arg
         50                  55                  60

Leu Gln Ser Glu Asn Asp Asn Arg Gly Gln Ile Val Arg Val Glu Gly
 65                  70                  75                  80

Glu Leu Asp Ile Val Arg Pro Pro Thr Ser Ile Gln Glu Glu Ser Gln
                 85                  90                  95

Glu Gln Gly Gly Arg Gly Gly Arg Tyr Tyr Ser Asn Gly Val Glu
                100                 105                 110

Glu Thr Phe Cys Ser Met Arg Leu Ile Glu Asn Ile Gly Asp Pro Ser
            115                 120                 125

Arg Ala Asp Ile Phe Thr Pro Glu Ala Gly Arg Val Arg Ser Leu Asn
        130                 135                 140
```

```
Ser His Asn Leu Pro Val Leu Gln Trp Ile Gln Leu Ser Ala Glu Arg
145                 150                 155                 160

Gly Val Leu Tyr Asn
                165

<210> SEQ ID NO 12
<211> LENGTH: 141
<212> TYPE: PRT
<213> ORGANISM: Linum usitatissimum

<400> SEQUENCE: 12

Glu Ala Ile Arg Leu Pro His Trp Asn Ile Asn Ala His Ser Ile Val
1               5                   10                  15

Tyr Ala Ile Arg Gly Gln Ala Arg Val Gln Ile Val Asn Glu Glu Gly
            20                  25                  30

Asn Ser Val Phe Asp Gly Val Leu Gln Glu Gly Gln Val Val Thr Val
        35                  40                  45

Pro Gln Asn Phe Ala Val Val Lys Arg Ser Gln Ser Glu Arg Phe Glu
    50                  55                  60

Trp Val Ala Phe Lys Thr Asn Asp Asn Ala Met Val Asn Ser Leu Ala
65                  70                  75                  80

Gly Arg Thr Ser Ala Val Arg Ala Ile Pro Ala Asp Val Leu Ala Asn
                85                  90                  95

Ala Trp Arg Val Ser Pro Glu Glu Ala Arg Val Lys Phe Asn Arg
            100                 105                 110

Gln Glu Thr His Leu Ala Ser Thr Arg Gly Ser Arg Ser Pro Gly
        115                 120                 125

Arg Leu Asn Val Val Lys Glu Val Ile Asn Leu Leu Met
    130                 135                 140

<210> SEQ ID NO 13
<211> LENGTH: 11
<212> TYPE: PRT
<213> ORGANISM: Linum usitatissimum

<400> SEQUENCE: 13

Gln Gln Gln Gly Gln Gln Gln Gly Gln Gln Gln
1               5                   10

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 14
tccactatgt aggtcata                                                 18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 15
ctttaaggtg tgagagtc                                                 18

<210> SEQ ID NO 16
<211> LENGTH: 15
```

```
<212> TYPE: DNA
<213> ORGANISM: Artificial Sequence
<220> FEATURE:
<223> OTHER INFORMATION: Description of Artificial Sequence: Primer

<400> SEQUENCE: 16 agggtgatc gatta                                                    15

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 17
gatagaaccc acacgagc                                                18

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 18
tatctagact caagcatacg gacaagggt                                    29

<210> SEQ ID NO 19
<211> LENGTH: 6
<212> TYPE: DNA
<213> ORGANISM: Artificial Sequence
<220> FEATURE:
<223> OTHER INFORMATION: Description of Artificial Sequence: XbaI site

<400> SEQUENCE: 19 tctaga                                                              6

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 20
ggttatcatt gtatgaactg a                                            21

<210> SEQ ID NO 21
<211> LENGTH: 6
<212> TYPE: DNA
<213> ORGANISM: Artificial Sequence
<220> FEATURE:
<223> OTHER INFORMATION: Description of Artificial Sequence: NcoI site

<400> SEQUENCE: 21 ccatgg                                                              6

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 22
```

-continued

```
gcaagcttaa tgtgacggtg aaataataac gg                              32

<210> SEQ ID NO 23
<211> LENGTH: 6
<212> TYPE: DNA
<213> ORGANISM: Artificial Sequence
<220> FEATURE:
<223> OTHER INFORMATION: Description of Artificial Sequence: HindIII
      Site

<400> SEQUENCE: 23 aagctt                                                            6

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 24
taggtacctg gcaggtaaag actctgctc                                  29

<210> SEQ ID NO 25
<211> LENGTH: 6
<212> TYPE: DNA
<213> ORGANISM: Artificial Sequence
<220> FEATURE:
<223> OTHER INFORMATION: Description of Artificial Sequence: KpnI Site

<400> SEQUENCE: 25 ggtacc                                                            6
```

We claim:

1. A method for the expression of a nucleic acid sequence of interest in flax seeds comprising:
   (a) preparing a chimeric nucleic acid construct comprising in the 5' to 3' direction of transcription as operably linked components:
      (1) a seed-preferred promoter obtained from flax wherein said seed-preferred promoter comprises the nucleic acid sequence as shown in FIG. 4 (SEQ ID NO: 8); and
      (2) said nucleic acid sequence of interest wherein said nucleic acid of interest is non-native to said seed-preferred promoter;
   (b) inducing said chimeric nucleic acid construct into a flax plant cell; and
   (c) regenerating a mature flax plant from said flax plant cell, wherein said nucleic acid sequence of interest is expressed in the seed of said flax plant.

2. The method according to claim 1 wherein expression of said nucleic acid sequence of interest results in an alteration in protein or fatty acid composition in said seed.

3. Transgenic flax seed prepared according to a method comprising:
   (a) preparing a chimeric nucleic acid construct comprising in the 5' to 3' direction of transcription as operably linked components:
      (1) a seed-preferred promoter obtained from flax wherein said seed-preferred promoter comprises the nucleic acid sequence as shown in FIG. 4 (SEQ ID NO: 8); and
      (2) a nucleic acid sequence of interest wherein said nucleic acid of interest is non-native to said seed-preferred promoter;
   (b) introducing said chimeric nucleic acid construct into a flax plant cell;
   (c) regenerating a mature flax plant from said flax plant cell, wherein said nucleic acid sequence of interest is expressed in the seed of said flax plant; and
   (d) harvesting seed from said mature flax plant.

4. Transgenic flax seed according to claim 3 wherein expression of said non-native gene of interest results in an alteration in the seed protein or fatty acid composition.

5. A transgenic flax plant capable of setting seed prepared by a method comprising:
   (a) preparing a chimeric nucleic acid construct comprising in the 5' to 3' direction of transcription as operably linked components:
      (1) a seed-preferred promoter obtained from flax wherein said seed-preferred promoter comprises the nucleic acid sequence as shown in FIG. 4 (SEQ ID NO: 8); and
      (2) a nucleic acid sequence of interest wherein said nucleic acid of interest is non-native to said seed-preferred promoter;
   (b) introducing said chimeric nucleic acid construct into a flax plant cell; and
   (c) regenerating a mature flax plant from said flax plant cell, wherein said nucleic acid sequence of interest is expressed in the seed of said flax plant.

6. An isolated nucleic acid molecule comprising:
   (a) the nucleic acid sequence as shown in FIG. 4 (SEQ ID NO: 8) wherein; or
   (b) a nucleic acid sequence that is complementary to the nucleic acid sequence of (a).

7. A chimeric nucleic acid molecule comprising;
(a) a seed-preferred promoter obtained from flax which comprises:
the nucleic acid sequence as shown in FIG. 4 (SEQ ID NO: 8) and
(b) a second nucleic acid sequence non-native to said flax seed-preferred promoter.

8. A method for the expression of a nucleic acid sequence of interest in a plant seed comprising:
(a) introducing the chimeric nucleic acid molecule according to claim 7 into a plant cell; and
(b) regenerating a mature plant from said plant cell, wherein the second nucleic acid sequence is expressed in the seed of said plant.

9. A method according to claim 8 wherein said plant cell is plant cell selected from the group consisting of soybean (*Glycine max*), rapeseed (*Brassica napus, Brassica campestris*), sunflower (*Helianthus annuus*), cotton (*Gossypium hirsutum*), corn (*Zea mays*), tobacco (*Nicotiana tobacum*), alfalfa (*Medicago sativa*), wheat (Triticum sp.), barley (*Hordeum vulgare*), oats (*Avena sativa L.*), sorghum (*Sorghum bicolor*), Arabidopsis thiliana, potato (Solanum sp.), flax/linseed (*Linum usitatissimum*), safflower (*Carthamus tinctorius*), oil palm (*Eleais guineeis*), groundnut (*Arachis hypogaea*), Brazil nut (*Bertholletia excelsa*) coconut (*Cocus nucifera*), castor (*Ricinus communis*), coriander (*Coriandrum sativum*) squash (*Cucurbita maxima*), jojoba (*Simmondsia chinensis*) and rice (*Oryza sativa*).

10. A method of making a transgenic plant comprising:
(a) introducing the chimeric nucleic acid molecule according to claim 7 into a plant cell; and
(b) regenerating a transgenic plant form said plant cell.

11. A transgenic plant prepared according to the method of claim 10.

12. A plant cell comprising the chimeric nucleic acid sequence according to claim 7.

13. Plant sees comprising the chimeric nucleic acid sequence according to claim 7.

14. Transgenic plant seed obtained from the plant according to claim 11.

15. A recombinant expression vector comprising the promoter according to claim 6.

16. A recombinant expression vector comprising the chimeric nucleic acid molecule according to claim 7.

* * * * *

UNITED STATES PATENT AND TRADEMARK OFFICE
CERTIFICATE OF CORRECTION

PATENT NO. : 6,777,591 B1
DATED : August 17, 2004
INVENTOR(S) : Sarita Chaudhary et al.

It is certified that error appears in the above-identified patent and that said Letters Patent is hereby corrected as shown below:

Title page,
Item [75], Inventors, replace "Maurico Moloney" with -- Maurice Moloney --; and replace "Surindor Singh" with -- Surinder Singh --;

Column 51,
Line 49, replace "inducing" with -- introducing --.

Signed and Sealed this

First Day of February, 2005

JON W. DUDAS
*Director of the United States Patent and Trademark Office*

UNITED STATES PATENT AND TRADEMARK OFFICE
CERTIFICATE OF CORRECTION

PATENT NO. : 6,777,591 B1  Page 1 of 1
APPLICATION NO. : 09/645593
DATED : August 17, 2004
INVENTOR(S) : Sarita Chaudhary et al.

It is certified that error appears in the above-identified patent and that said Letters Patent is hereby corrected as shown below:

In column 51, line 45 claim 1, part (a)(1), replace "as shown in FIG. 4 (SEQ ID NO: 8);" with --as shown in FIG. 4 (SEQ ID NO: 8) from nucleotides 1 to 2035;-- ;

Column 51, line 64 claim 3, part (a)(1), replace "as shown in FIG. 4 (SEQ ID NO: 8);" with --as shown in FIG. 4 (SEQ ID NO: 8) from nucleotides 1 to 2035;-- .

In column 52, line 54 claim 5, part (a)(1), replace "as shown in FIG. 4 (SEQ ID NO: 8);" with --as shown in FIG. 4 (SEQ ID NO: 8) from nucleotides 1 to 2035;-- ;

Column 52, line 64-65 claim 6, part (a), replace "as shown in FIG. 4 (SEQ ID NO: 8);" with --as shown in FIG. 4 (SEQ ID NO: 8) from nucleotides 1 to 2035;-- .

In column 53, line 4-5 claim 7, part (a), replace "as shown in FIG. 4 (SEQ ID NO: 8);" with --as shown in FIG. 4 (SEQ ID NO: 8) from nucleotides 1 to 2035;-- .

Signed and Sealed this

Twentieth Day of February, 2007

JON W. DUDAS
*Director of the United States Patent and Trademark Office*